US011197696B2

(12) United States Patent
Jackson

(10) Patent No.: US 11,197,696 B2
(45) Date of Patent: *Dec. 14, 2021

(54) PIVOTAL BONE ANCHOR ASSEMBLY WITH THREADED SPHERICAL SHANK HEAD HAVING A PLANAR TOP SURFACE

(71) Applicant: Roger P. Jackson, Prairie Village, KS (US)

(72) Inventor: Roger P. Jackson, Prairie Village, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/172,317

(22) Filed: Feb. 10, 2021

(65) Prior Publication Data

US 2021/0161564 A1 Jun. 3, 2021

Related U.S. Application Data

(63) Continuation of application No. 17/069,205, filed on Oct. 13, 2020, now Pat. No. 11,051,856, which is a
(Continued)

(51) Int. Cl.
*A61B 17/70* (2006.01)
*A61B 17/86* (2006.01)

(52) U.S. Cl.
CPC ...... *A61B 17/7037* (2013.01); *A61B 17/7032* (2013.01); *A61B 17/86* (2013.01); *A61B 2560/0406* (2013.01)

(58) Field of Classification Search
CPC ... A61B 17/7008; A61B 17/86; A61B 17/701; A61B 17/702; A61B 17/7022;
(Continued)

(56) References Cited

U.S. PATENT DOCUMENTS 1,646,143 A  10/1927  Forster
2,376,089 A   5/1945  Savageau
(Continued)

FOREIGN PATENT DOCUMENTS

DE   19507141      9/1996
DE   20207850 U1  10/2002
(Continued)

OTHER PUBLICATIONS

European Search Report, EP14189707.4, dated Feb. 25, 2015.
(Continued)

*Primary Examiner* — Pedro Philogene
(74) *Attorney, Agent, or Firm* — Polsinelli PC

(57) ABSTRACT

A pivotal bone anchor assembly includes a receiver with a base defining an internal cavity with a seating surface adjacent a bottom opening and an upper portion defining a channel configured to receive an elongate rod. The assembly also includes an anchor member having a proximal end portion with a lower contact surface slidably engageable with the seating surface to establish pivotable motion between the anchor member and the receiver, and a planar upper surface surrounding an internal drive socket. The assembly further includes an insert positionable within the channel with a lower surface engageable with the proximal end portion of the anchor member to direct a downwardly-directed force onto the proximal end portion to lock the position of the anchor member relative to the receiver, with the planar upper surface remaining spaced apart from the lower surface of the insert so as to not directly receive the downwardly-directed force therefrom.

29 Claims, 15 Drawing Sheets

Related U.S. Application Data continuation of application No. 16/738,638, filed on Jan. 9, 2020, now Pat. No. 10,799,272, which is a continuation of application No. 16/403,950, filed on May 6, 2019, now Pat. No. 10,561,445, which is a continuation of application No. 15/960,792, filed on Apr. 24, 2018, now Pat. No. 10,278,740, which is a continuation-in-part of application No. 15/723,972, filed on Oct. 3, 2017, now Pat. No. 11,000,314, which is a continuation of application No. 14/868,213, filed on Sep. 28, 2015, now Pat. No. 9,808,292, which is a continuation-in-part of application No. 13/068,505, filed on May 12, 2011, now Pat. No. 9,144,444, which is a continuation of application No. 12/290,244, filed on Oct. 29, 2008, now Pat. No. 7,967,850.

(60) Provisional application No. 61/000,964, filed on Oct. 30, 2007.

(58) Field of Classification Search
CPC ............ A61B 17/7029; A61B 17/7031; A61B 17/7032; A61B 17/7035; A61B 17/7034; A61B 17/7037; A61B 2560/0406
See application file for complete search history.

(56) References Cited

U.S. PATENT DOCUMENTS

| | | |
|---|---|---|
| 5,312,404 A | 5/1994 | Asher et al. |
| 5,360,431 A | 11/1994 | Puno et al. |
| 5,429,639 A | 7/1995 | Judet |
| 5,443,467 A | 8/1995 | Biedermann et al. |
| 5,466,237 A | 11/1995 | Byrd, III et al. |
| 5,476,464 A | 12/1995 | Metz-Stavenhagen et al. |
| 5,545,163 A | 8/1996 | Miller |
| 5,562,661 A | 10/1996 | Yoshimi et al. |
| 5,591,166 A | 1/1997 | Bernhardt et al. |
| 5,601,553 A | 2/1997 | Trebing et al. |
| 5,667,508 A | 9/1997 | Errico et al. |
| 5,669,911 A | 9/1997 | Errico et al. |
| 5,672,176 A | 9/1997 | Biedermann et al. |
| 5,690,630 A | 11/1997 | Errico et al. |
| 5,716,356 A | 2/1998 | Biedermann et al. |
| 5,725,528 A | 3/1998 | Errico et al. |
| 5,733,286 A | 3/1998 | Errico et al. |
| 5,782,833 A | 7/1998 | Haider |
| 5,800,435 A | 9/1998 | Errico et al. |
| 5,817,094 A | 10/1998 | Errico et al. |
| 5,879,350 A | 3/1999 | Sherman et al. |
| 5,891,145 A | 4/1999 | Morrison et al. |
| 5,899,906 A | 5/1999 | Schenk |
| 5,954,725 A | 9/1999 | Sherman et al. |
| 6,019,759 A | 2/2000 | Rogozinski |
| 6,050,997 A | 4/2000 | Mullane |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,090,110 A | 7/2000 | Metz-Stavenhagen |
| 6,090,111 A | 7/2000 | Nichols |
| 6,132,432 A | 10/2000 | Richelsoph |
| 6,146,383 A | 11/2000 | Studer et al. |
| 6,187,005 B1 | 2/2001 | Brace et al. |
| RE37,161 E | 5/2001 | Michelson et al. |
| 6,224,596 B1 | 5/2001 | Jackson |
| 6,254,602 B1 | 7/2001 | Justis |
| 6,273,888 B1 | 8/2001 | Justis |
| 6,280,442 B1 | 8/2001 | Barker et al. |
| 6,287,308 B1 | 9/2001 | Betz et al. |
| 6,287,311 B1 | 9/2001 | Sherman et al. |
| 6,302,888 B1 | 10/2001 | Mellinger et al. |
| 6,328,739 B1 | 12/2001 | Liu et al. |
| 6,368,321 B1 | 4/2002 | Jackson |
| 6,488,681 B2 | 12/2002 | Martin et al. |
| 6,565,565 B1 | 5/2003 | Yuan et al. |
| 6,716,214 B1 | 4/2004 | Jackson |
| 6,835,196 B2 | 12/2004 | Biedermann et al. |
| 6,964,666 B2 | 11/2005 | Jackson |
| 7,250,052 B2 | 7/2007 | Landry et al. |
| 7,332,981 B2 | 1/2008 | Jackson |
| 7,491,218 B2 | 2/2009 | Landry et al. |
| 7,513,905 B2 | 4/2009 | Jackson |
| 7,572,279 B2 | 8/2009 | Jackson |
| 7,625,396 B2 | 12/2009 | Jackson |
| 7,662,175 B2 | 2/2010 | Jackson |
| 7,776,067 B2 | 8/2010 | Jackson |
| 7,833,250 B2 | 11/2010 | Jackson |
| 7,967,850 B2 | 6/2011 | Jackson |
| 8,137,386 B2 | 3/2012 | Jackson |
| 8,162,989 B2* | 4/2012 | Khalili ............... A61B 17/7032 606/266 |
| 8,192,440 B2 | 6/2012 | Jones et al. |
| 8,603,145 B2 | 12/2013 | Forton et al. |
| 9,066,762 B2 | 6/2015 | Jones |
| 9,144,444 B2 | 9/2015 | Jackson |
| RE46,431 E | 6/2017 | Jackson |
| 9,808,292 B2 | 11/2017 | Jackson |
| 10,278,740 B2* | 5/2019 | Jackson ............. A61B 17/7032 |
| 10,335,200 B2 | 7/2019 | Jackson |
| 10,561,444 B2 | 2/2020 | Jackson |
| 10,561,445 B2* | 2/2020 | Jackson ................. A61B 17/86 |
| 10,799,272 B2* | 10/2020 | Jackson ................. A61B 17/86 |
| 2001/0001119 A1 | 5/2001 | Lombardo |
| 2002/0026193 A1 | 2/2002 | Barker et al. |
| 2003/0023240 A1 | 1/2003 | Amrein et al. |
| 2003/0100904 A1 | 5/2003 | Biedermann |
| 2003/0187434 A1 | 10/2003 | Lin |
| 2004/0153068 A1 | 8/2004 | Janowski et al. |
| 2004/0236330 A1 | 11/2004 | Purcell et al. |
| 2005/0216003 A1 | 9/2005 | Biedermann et al. |
| 2005/0267472 A1 | 12/2005 | Biedermann et al. |
| 2005/0277928 A1 | 12/2005 | Boschert |
| 2006/0084979 A1 | 4/2006 | Jackson |
| 2006/0173456 A1 | 8/2006 | Hawkes et al. |
| 2006/0247631 A1 | 11/2006 | Ahn et al. |
| 2007/0073291 A1 | 3/2007 | Cordaro et al. |
| 2008/0009862 A1 | 1/2008 | Hoffman |
| 2008/0015580 A1* | 1/2008 | Chao .................. A61B 17/7037 606/86 A |
| 2008/0269809 A1 | 10/2008 | Garamszegi |
| 2008/0312655 A1 | 12/2008 | Kirschman et al. |
| 2010/0030280 A1 | 2/2010 | Jackson |
| 2010/0036433 A1 | 2/2010 | Jackson |
| 2017/0196610 A1 | 7/2017 | Jackson |
| 2018/0021067 A1 | 1/2018 | Jackson |
| 2020/0022738 A1 | 1/2020 | Jackson |

FOREIGN PATENT DOCUMENTS

| | | |
|---|---|---|
| EP | 1121902 | 1/2001 |
| WO | WO 95/13755 | 5/1995 |

OTHER PUBLICATIONS

*EBI Omega 21 Brochure*, EBI Spine Systems, pub. 1999.
*Claris Instrumentation Brochure*, G Med, pub. 1997.
*VLS System Variable Locking Screw Brochure*, Interpore Cross International, 1999.
*The Rod Plate System Brochure*, Stryker Howmedica Osteonics, pub. Oct. 1999.
*SDRS Surgical Dynamics Rod System Brochure*, Surgical Dynamics, pub. 1998-99.
*Versalok Low Back Fixation System Brochure*, Wright Medical Technology, Inc., pub. 1997.

* cited by examiner

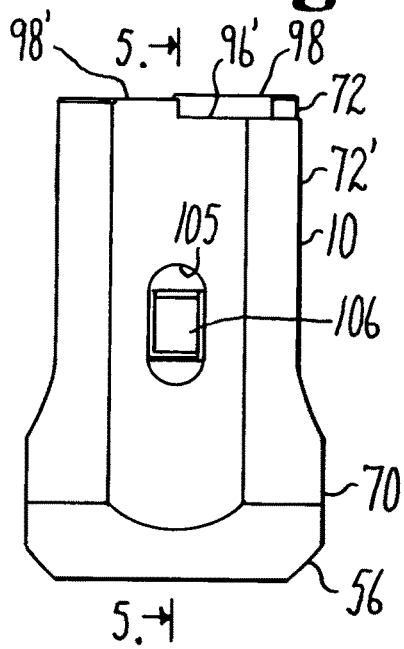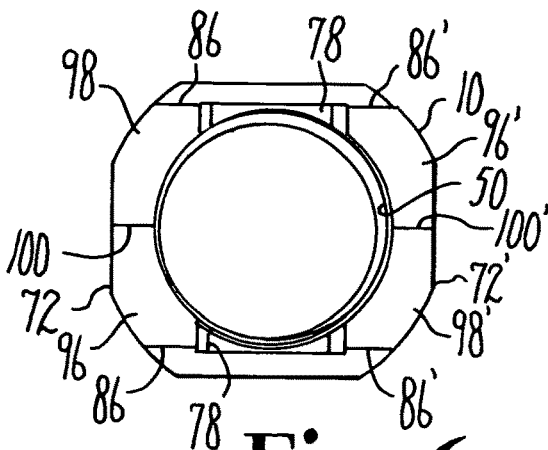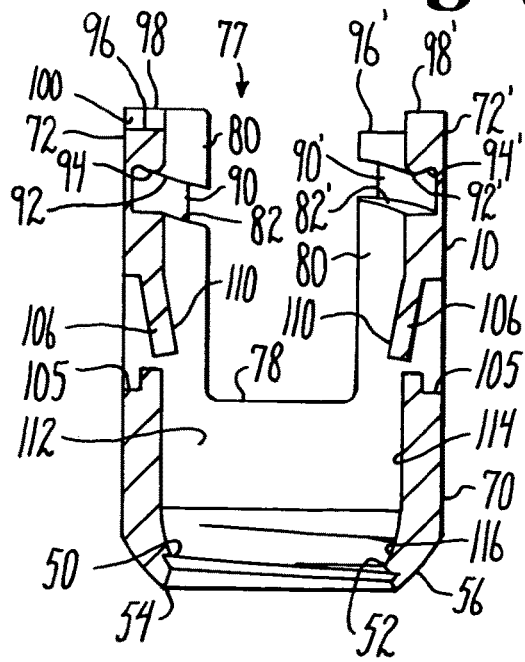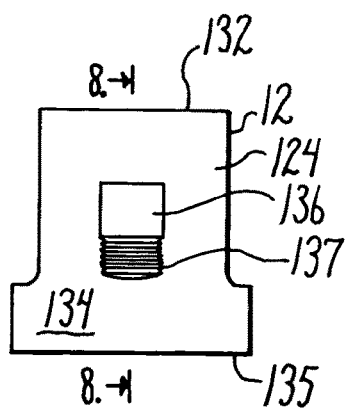

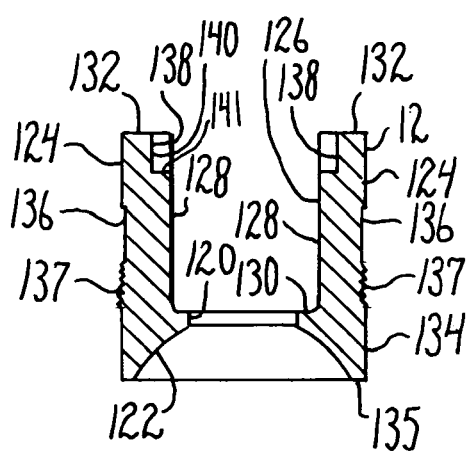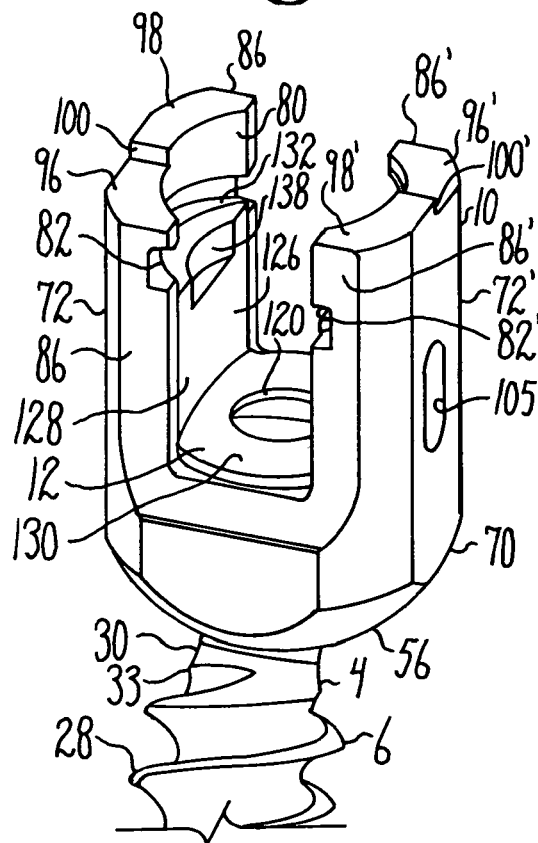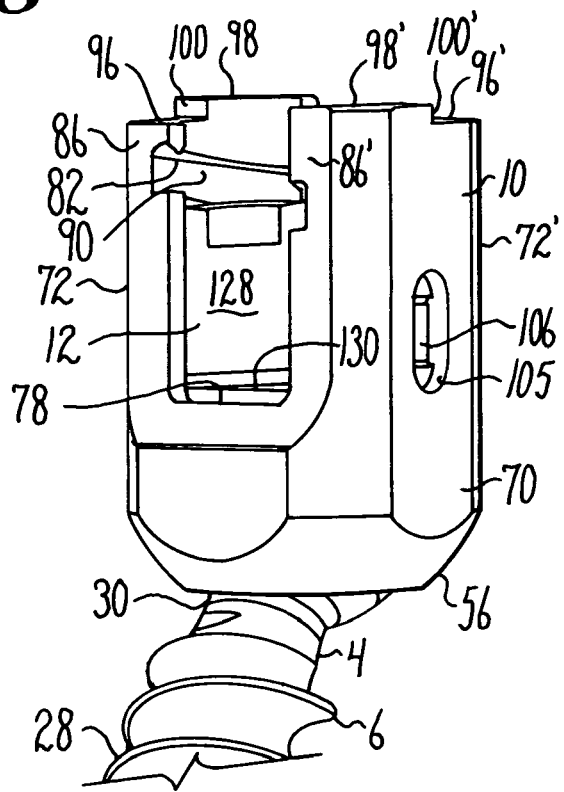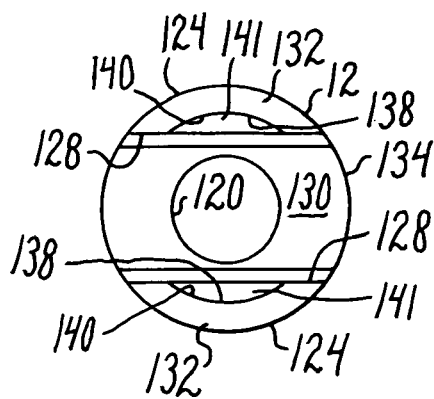

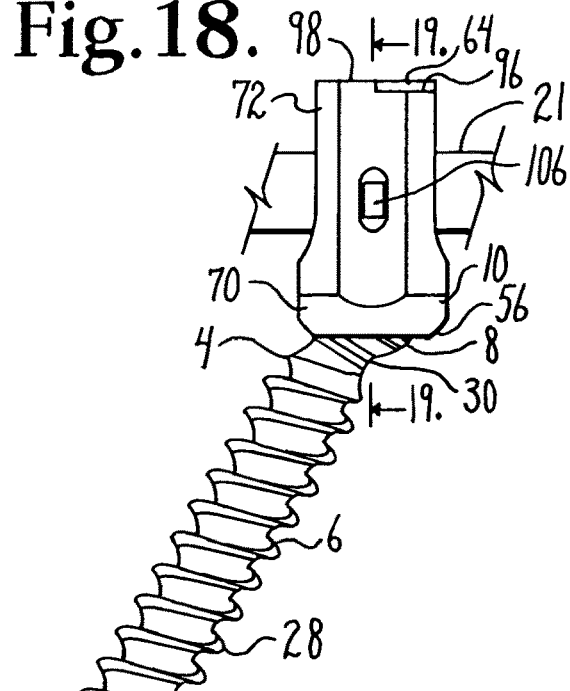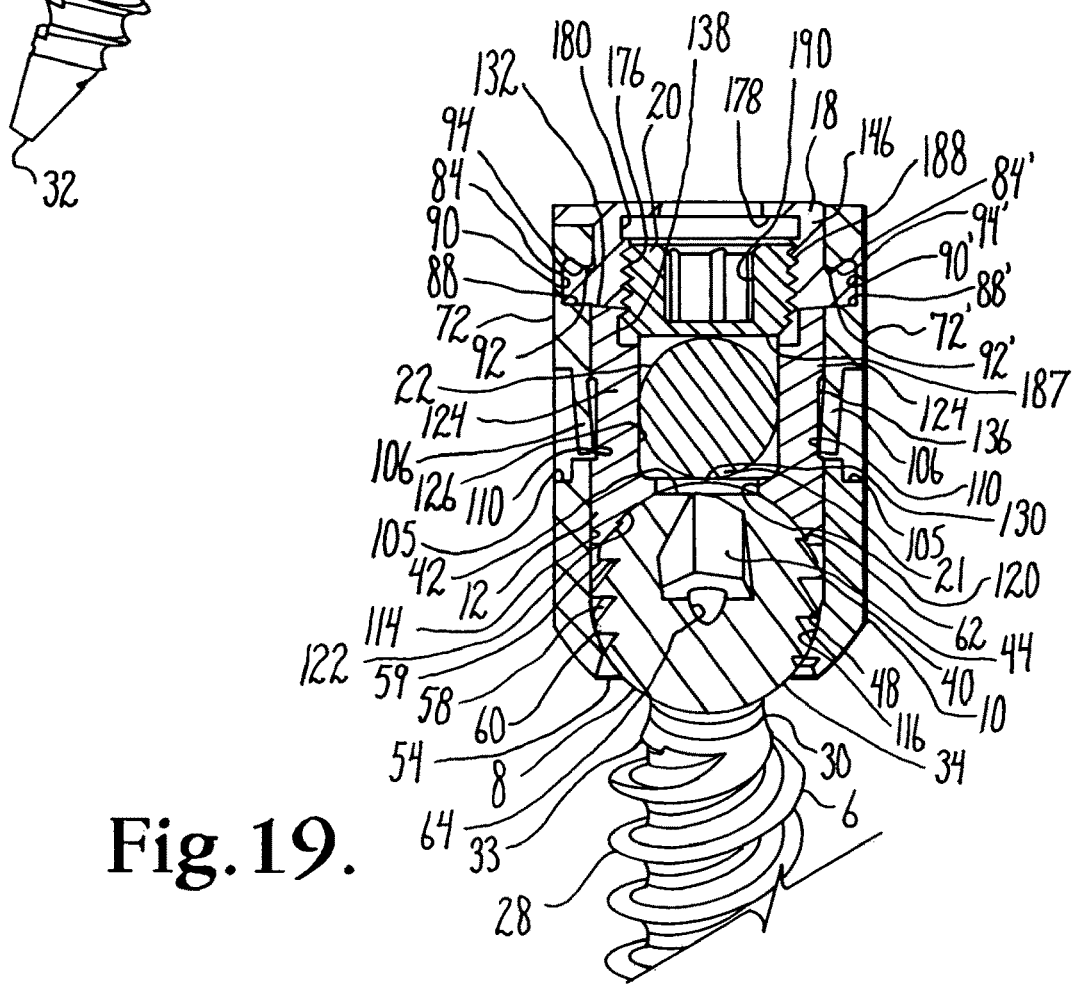

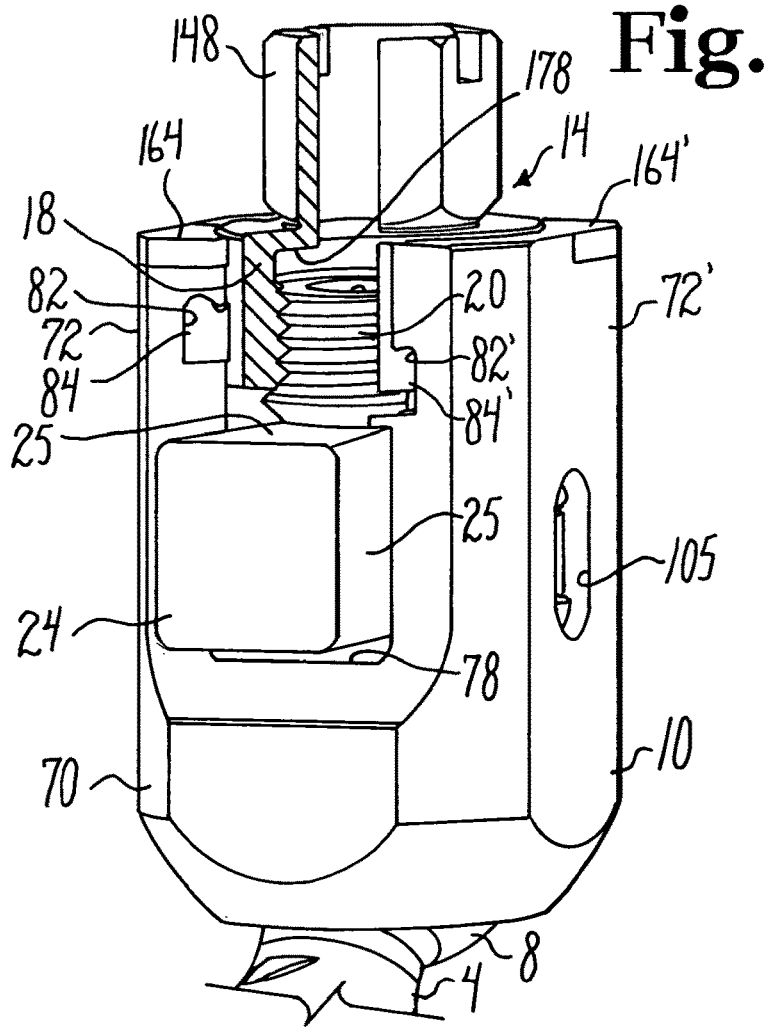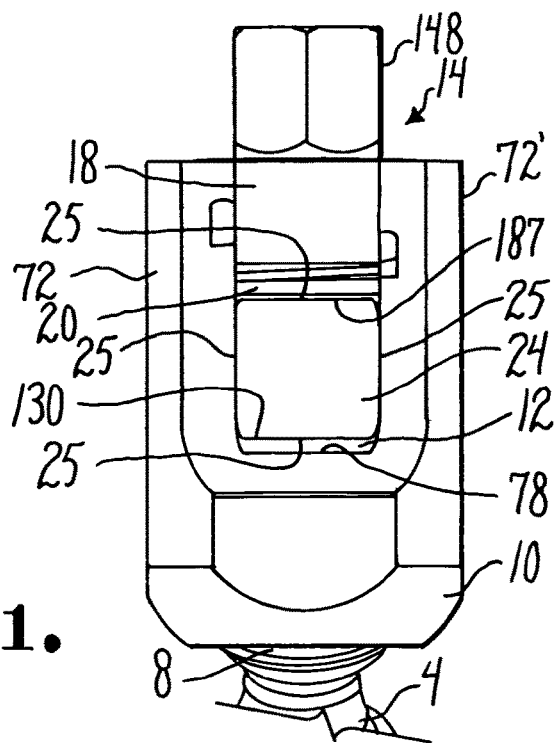

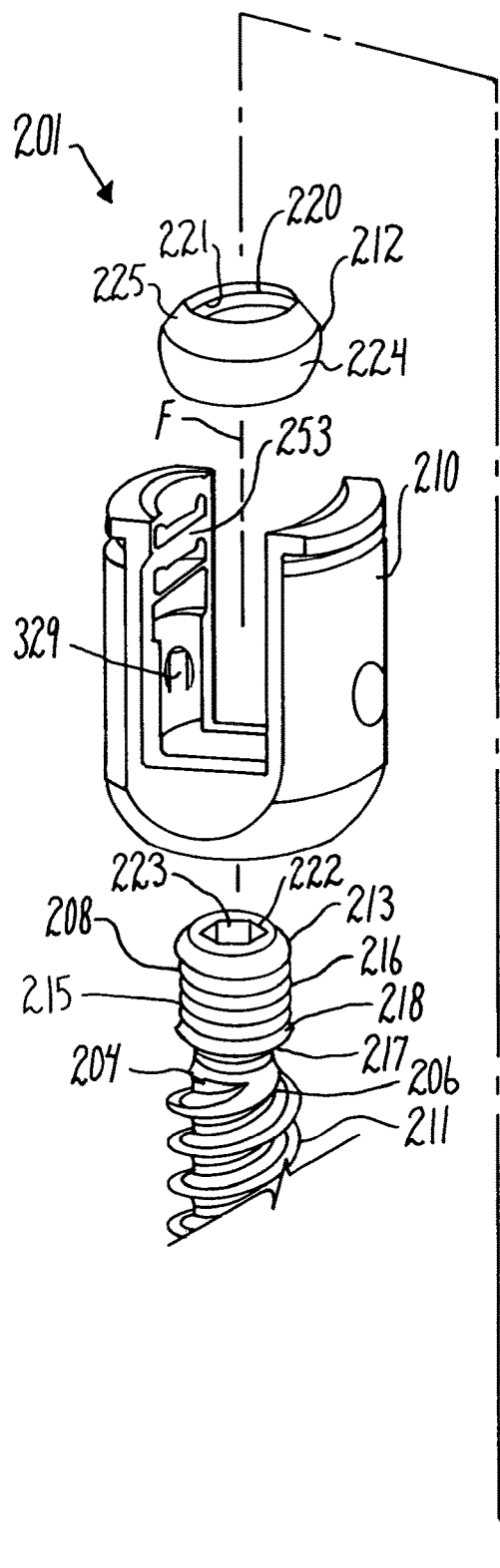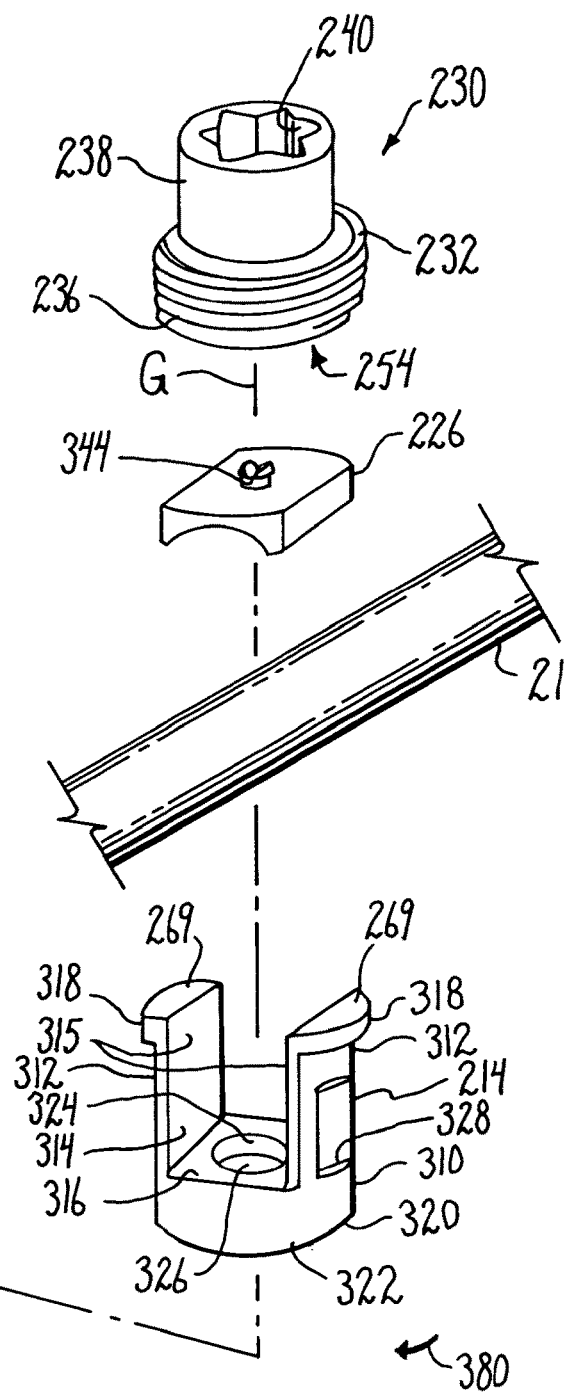
Fig. 22.

Fig.23.
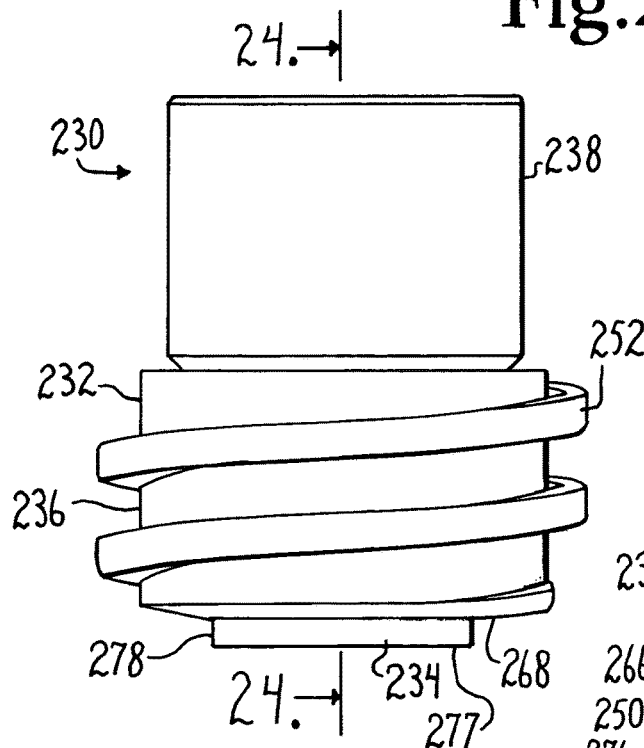
Fig.24.
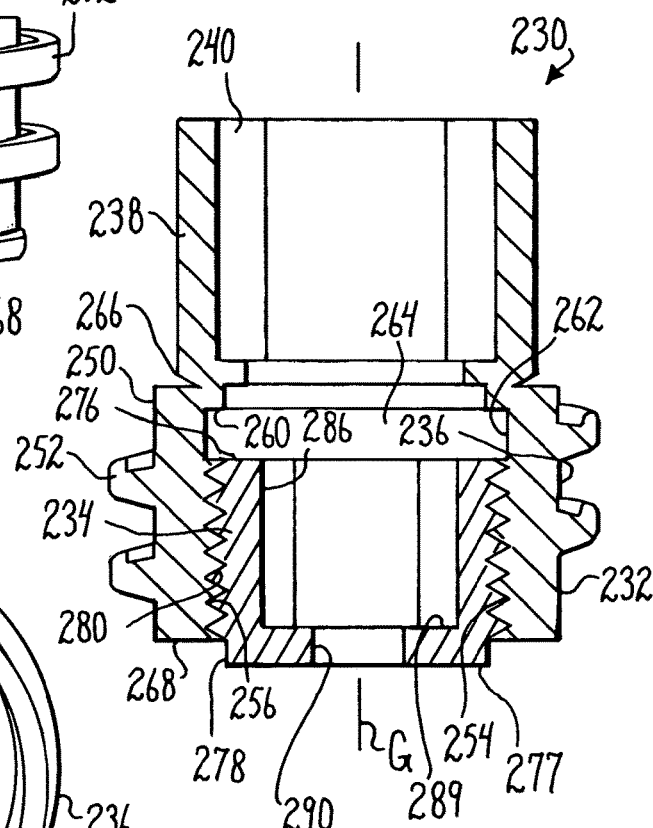
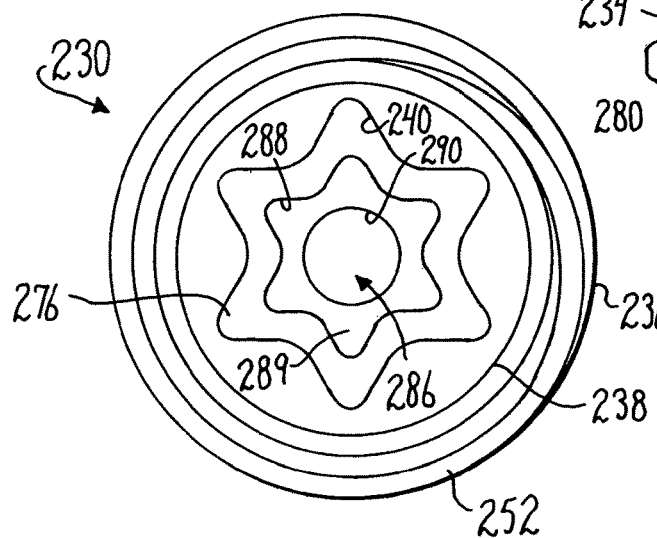
Fig.25.

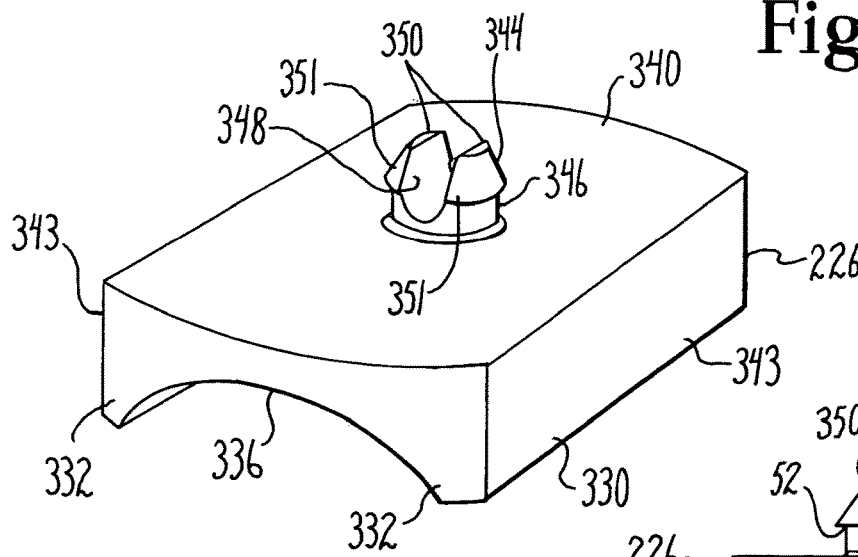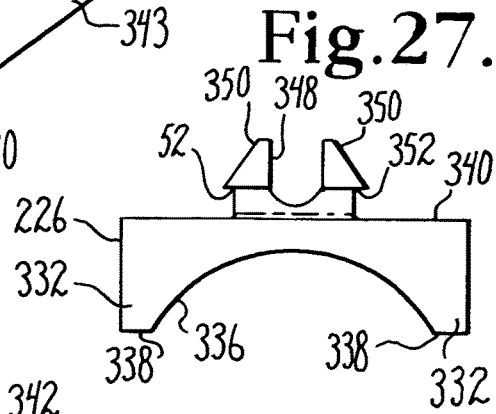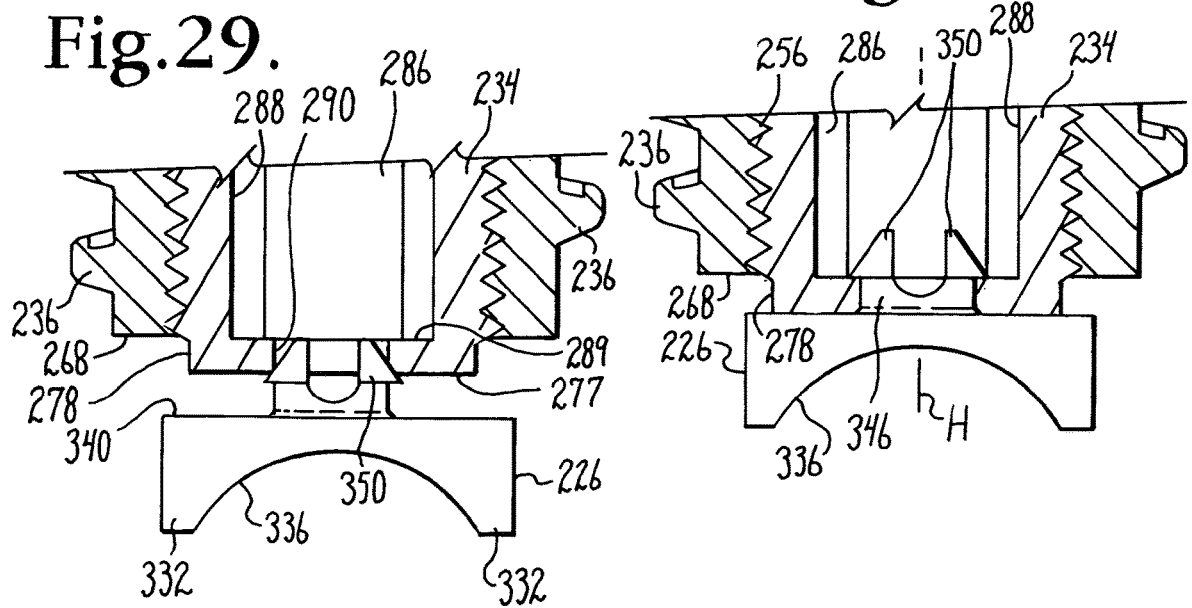

Fig. 31.
Fig. 32.
Fig. 33.
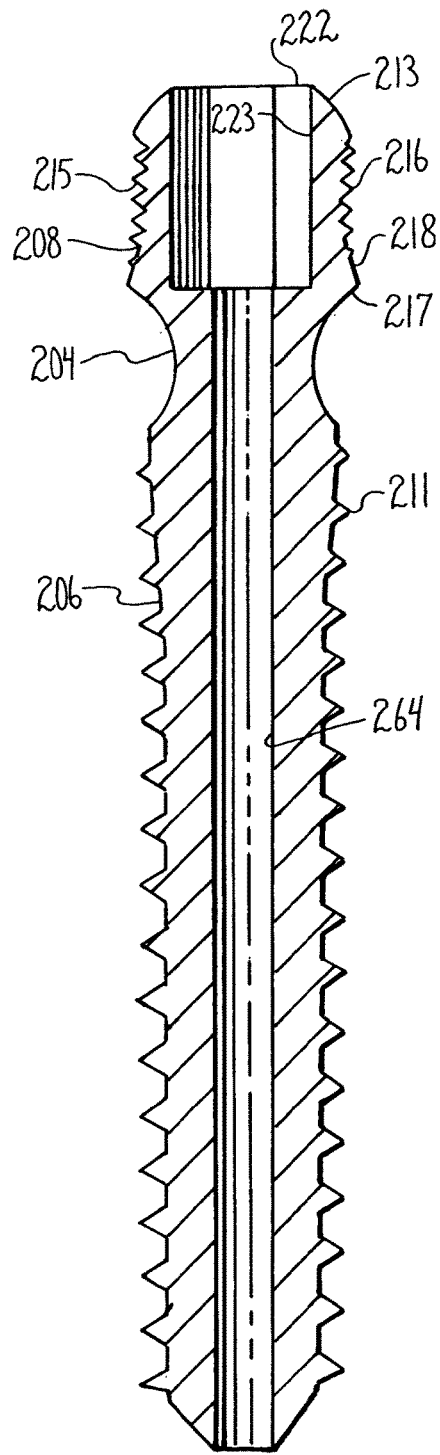
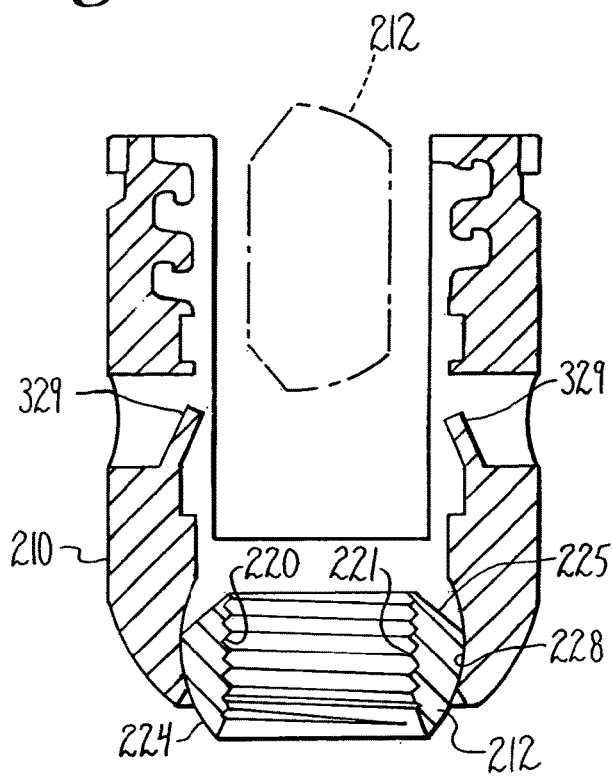
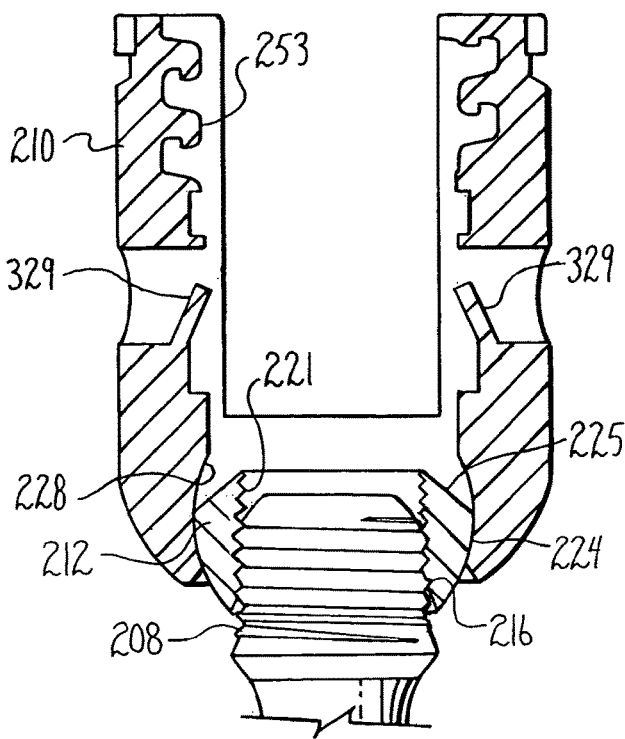

Fig.34.
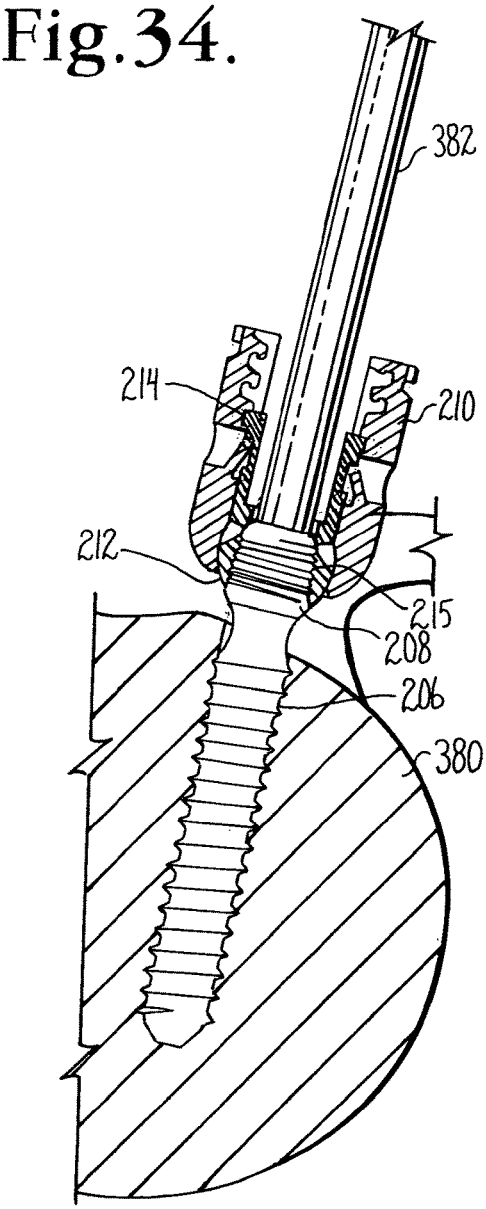
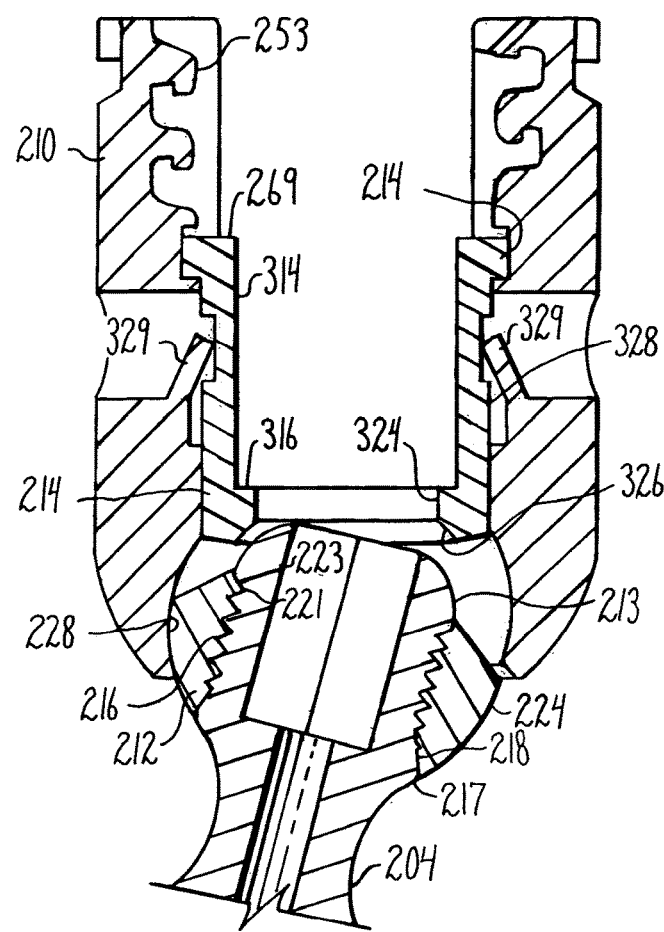
Fig.35.

PIVOTAL BONE ANCHOR ASSEMBLY WITH THREADED SPHERICAL SHANK HEAD HAVING A PLANAR TOP SURFACE

CROSS REFERENCE TO RELATED APPLICATIONS

This application is a continuation of U.S. patent application Ser. No. 17/069,205 filed Oct. 13, 2020, which is a continuation of U.S. patent application Ser. No. 16/738,638, filed Jan. 9, 2020, now U.S. Pat. No. 10,799,272, which is a continuation of U.S. patent application Ser. No. 16/403,950, filed May 6, 2019, now U.S. Pat. No. 10,561,445, which is a continuation of U.S. patent application Ser. No. 15/960,792, filed Apr. 24, 2018, now U.S. Pat. No. 10,278,740, which is a continuation-in-part of U.S. patent application Ser. No. 15/723,972, filed Oct. 3, 2017, which is a continuation of U.S. patent application Ser. No. 14/868,213, filed Sep. 28, 2015, now U.S. Pat. No. 9,808,292, which is a continuation-in-part of U.S. patent application Ser. No. 13/068,505, filed May 12, 2011, now U.S. Pat. No. 9,144,444, which is a continuation of U.S. patent application Ser. No. 12/290,244, filed Oct. 29, 2008, now U.S. Pat. No. 7,967,850, which claims the benefit of U.S. Provisional Application No. 61/000,964, filed Oct. 30, 2007, each of which is incorporated by reference in its entirety herein and for all purposes. U.S. Pat. No. 7,967,850 has since been reissued from U.S. patent application Ser. No. 14/460,607, filed Aug. 15, 2017, as U.S. Pat. No. RE46,431, which is incorporated by reference in its entirety herein and for all purposes.

BACKGROUND OF THE INVENTION

The present invention is directed to polyaxial bone screws for use in bone surgery, particularly spinal surgery, and cooperating elongate connecting members that are at least somewhat plastically deformable. Such screws have a receiver or head that can swivel about a shank of the bone screw, allowing the receiver to be positioned in any of a number of angular configurations relative to the shank.

Many spinal surgery procedures require securing various implants to bone and especially to vertebrae along the spine. For example, elongate members, such as solid rigid rods are often utilized that extend along the spine to provide support to vertebrae that have been damaged or weakened due to injury or disease. Such elongate members must be supported by certain vertebrae and support other vertebrae.

The most common mechanism for providing vertebral support is to implant bone screws into certain bones which then in turn support the elongate member or are supported by the elongate member. Bone screws of this type may have a fixed head or receiver relative to a shank thereof. In the fixed bone screws, the head cannot be moved relative to the shank and the rod or other elongate member must be favorably positioned in order for it to be placed within the head. This is sometimes very difficult or impossible to do. Therefore, polyaxial bone screws are commonly preferred.

Polyaxial bone screws allow rotation of the receiver about the shank until a desired rotational position of the receiver is achieved relative to the shank. Thereafter, a rod or other elongate connecting member can be inserted into the receiver and eventually the rod and the receiver are locked or fixed in a particular position relative to the shank.

A variety of polyaxial or swivel-head bone screw assemblies are available. One type of bone screw assembly includes an open head or receiver that allows for placement of a rod or other elongate member within the receiver. A closure top or plug is then used to capture the rod in the receiver of the screw. Thus, the closure top or plug pressing against the rod not only locks the rod in place but also locks the bone screw shank in a desired angular position with respect to the receiver. A draw back to such a system occurs when the rod or other elongate connecting member is made from a material that exhibits creep or viscoelastic behavior. Creep is a term used to describe the tendency of a material to move, flow or to deform permanently to relieve stresses. Material deformation occurs as a result of long term exposure to levels of stress that are below the yield or ultimate strength of the material. Rods and other longitudinal connecting members made from polymers, such as polyetheretherketone (PEEK), especially pure PEEK and rubbers, have a greater tendency to exhibit creep, than, for example metals or metal alloys, such as stainless steel, titanium and nickel titanium (commonly referred to by its trade name Nitinol). When a rod or other longitudinal connecting member exhibits creep deformation over time, the closure top may no longer tightly engage the connecting member. This in itself is not necessarily problematic. However, such loosening also results in loosening of the frictional engagement between the receiver and the bone screw shank that locks the angular orientation of the shank with respect to the receiver. Body movement and stresses may then result in undesirable pivoting of the shank with respect to the receiver causing mis-alignment, greater stress and further loosening of the various polyaxial bone screw components.

It is known to equip a bone screw assembly with an upper and/or a lower pressure insert located within the receiver for engaging and closely holding one or more surfaces of a rod or other longitudinal connecting member. Nested closure tops are known in the art that include a fastening portion having an outer thread for engaging an interior threaded surface of the receiver arms and also an inner thread for engaging a threaded set screw. The fastening portion of the closure top is disposed within the receiver arms but does not operationally abut against a rod or other longitudinal connecting member. Rather, the fastening portion abuts against one or more pressure inserts also located in the receiver that in turn engage a polyaxial bone screw mechanism so that the shank may be set and locked at a desired angular position with respect to the receiver prior to locking the rod or other longitudinal connecting member in place by direct or indirect pressure thereon by the independently rotatable inner set screw. However, one of the drawbacks to such a polyaxial implant is that to maintain a relatively non-bulky, low profile assembly, the numerous inserts and other component parts of such an assembly have thin walls that provide the desired low profile but otherwise lack sufficient strength to withstand the stresses placed thereon by the human body and other component parts of the bone screw assembly. In order to remedy this problem, it is further known in the art to equip such an assembly with an outer nut (located outside of the receiver arms) to keep the arms of the receiver from splaying and aid in securely holding any inserts and other small component parts within the receiver of the bone screw assembly so that the parts do not loosen or disassemble within the body. However, such a nut adds undesirable bulk to the assembly and may lead to undesirable interference with vertebrae and other medical implants.

SUMMARY OF THE INVENTION

A polyaxial bone screw assembly of the present invention includes a shank having a generally elongate body with an upper end portion and a lower threaded portion for fixation to a bone. The bone screw assembly further includes a receiver having a top portion and a base. The top portion is open and has a channel. The base includes an inner seating surface partially defining a cavity and has a lower aperture or opening. The channel of the top portion communicates with the cavity, which in turn communicates with an opening to an exterior of the base. The shank upper portion is disposed in the receiver cavity and the shank extends through the receiver base opening. A shank capture connection is provided by the upper portion that includes a first helical guide and advancement structure that mates with a second helical guide and advancement structure on a retaining structure, the retaining structure configured for polyaxial motion with respect to the receiver. The shank has an upper surface that exclusively engages a compression insert that in turn engages a longitudinal connecting member being supported within the receiver. In certain embodiments, the compression insert includes a planar seat and spaced planar sides for closely receiving a variety of elongate connecting members including members having planar or cylindrical surfaces. A closure structure of the invention may be dual locking and include an outer fastener and an inner set screw. The outer fastener is sized and shaped for engaging the compression insert independent of the longitudinal connecting member for securing the assembly in a wide range of angular orientations. The inner set screw exclusively engages the longitudinal connecting member. In an illustrated embodiment the outer fastener includes a pair of opposed flanges for interlocking engagement with a pair of opposed flange tracks of the receiver. In another embodiment, the outer fastener includes an outer helical flange for interlocking engagement with a discontinuous helical guide and advancement structure located on the receiver.

Objects and Advantages of the Invention

Objects of the invention include one or more of the following: providing a polyaxial bone screw having a shank with an integral upper end portion that threadably mates with a retaining structure configured for polyaxial motion with respect to the receiver prior to locking; providing such a polyaxial bone screw that includes a pressure insert that exerts pressure exclusively on an upper surface of the integral and stronger shank upper end portion, the upper surface being substantially spaced from the retaining structure; providing such an implant wherein all of the parts remain together and do not separate; providing a lightweight, low profile polyaxial bone screw that assembles in such a manner that the components cooperate to create an overall structure that prevents unintentional disassembly; providing a polyaxial bone screw that provides independent locking for the bone screw shank and the longitudinal connecting member; providing such an assembly that includes a longitudinal connecting member that may be of non-circular or circular cross-section; providing such an assembly that remains in a locked position even if the longitudinal connecting member undergoes deformation such as creep; providing a polyaxial bone screw with features that provide adequate frictional or gripping surfaces for bone implantation tools and may be readily, securely fastened to each other and to bone; and providing apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 4 is an enlarged side elevational view of the receiver of FIG. 1.

FIG. 5 is an enlarged cross-sectional view taken along the line 5-5 of FIG. 4.

FIG. 6 is an enlarged top plan view of the receiver of FIG. 1.

FIG. 7 is an enlarged side elevational view of the lower compression insert of FIG. 1.

FIG. 8 is a cross-sectional view taken along the line 8-8 of FIG. 7.

FIG. 9 is an enlarged top plan view of the lower compression insert of FIG. 1.

FIG. 10 is an enlarged and partial perspective view of the shank, receiver and compression insert of FIG. 1, shown assembled.

FIG. 11 is a second enlarged and partial perspective view, similar to FIG. 10.

FIG. 17 is an enlarged and partial front elevational view of the assembly of FIG. 1 shown in a stage of assembly and with portions broken away to show the detail thereof.

FIG. 18 is an enlarged and partial side elevational view of the assembly of FIG. 1 shown fully assembled and with a break-off top removed.

FIG. 19 is a cross-sectional view taken along the line 19-19 of FIG. 18.

FIG. 20 is an enlarged and partial perspective view of the assembly of FIG. 1 shown with a bar in lieu of the rod shown in FIG. 1 and with portions broken away to show the detail thereof.

FIG. 21 is an enlarged and partial front elevational view of the assembly shown in FIG. 20.

FIG. 22 is an enlarged, partial and exploded perspective view of a second, alternative bone screw assembly according to the invention including a bone screw shank, a receiver, a retaining structure, a first lower compression insert, a second upper compression insert and a closure member and shown with a longitudinal connecting member in the form of a rod.

FIG. 23 is an enlarged front elevational view of the closure member of FIG. 22.

FIG. 24 is a cross-sectional view taken along the line 24-24 of FIG. 23.

FIG. 25 is an enlarged top plan view of the closure member of FIG. 23.

FIG. 26 is an enlarged perspective view of the upper compression insert of FIG. 22.

FIG. 27 is an enlarged front elevational view of the upper compression insert of FIG. 22.

FIG. 28 is an enlarged side elevational view of the upper compression insert of FIG. 22.

FIG. 29 is an enlarged and partial cross-sectional view of the closure member, similar to FIG. 24 and further showing the upper compression insert in front elevation prior to attachment to the closure member.

FIG. 30 is an enlarged and partial cross-sectional view of the closure member and front elevational view of the upper compression member, similar to FIG. 29, showing the upper compression member rotatably attached to the closure member.

FIG. 31 is an enlarged front elevational view of the bone screw shank of FIG. 22 with portions broken away to show the detail thereof.

FIG. 32 is an enlarged front elevational view of the receiver and retaining structure of FIG. 22 with portions broken away to show the detail thereof and further showing the retaining structure in phantom in an early step of assembly of the bone screw assembly of FIG. 22.

FIG. 33 is an enlarged and partial front elevational view of the receiver, the retaining structure and the bone screw shank of FIG. 22 with portions broken away to show the detail thereof and shown in a step of assembly subsequent to that shown in FIG. 32.

FIG. 34 is a reduced front elevational view of the receiver, the bone screw shank and the retaining structure of FIG. 22 with portions broken away to show the detail thereof and shown with a tool driving the bone screw shank into a vertebrae, also with portions broken away to show the detail thereof.

FIG. 35 is an enlarged and partial front elevational view of the receiver, bone screw shank, retaining structure and lower compression insert of FIG. 22 with portions broken away to show the detail thereof and shown with the rod illustrated in FIG. 22, also with portions broken away to show the detail thereof.

DETAILED DESCRIPTION OF THE INVENTION

Figure 1:
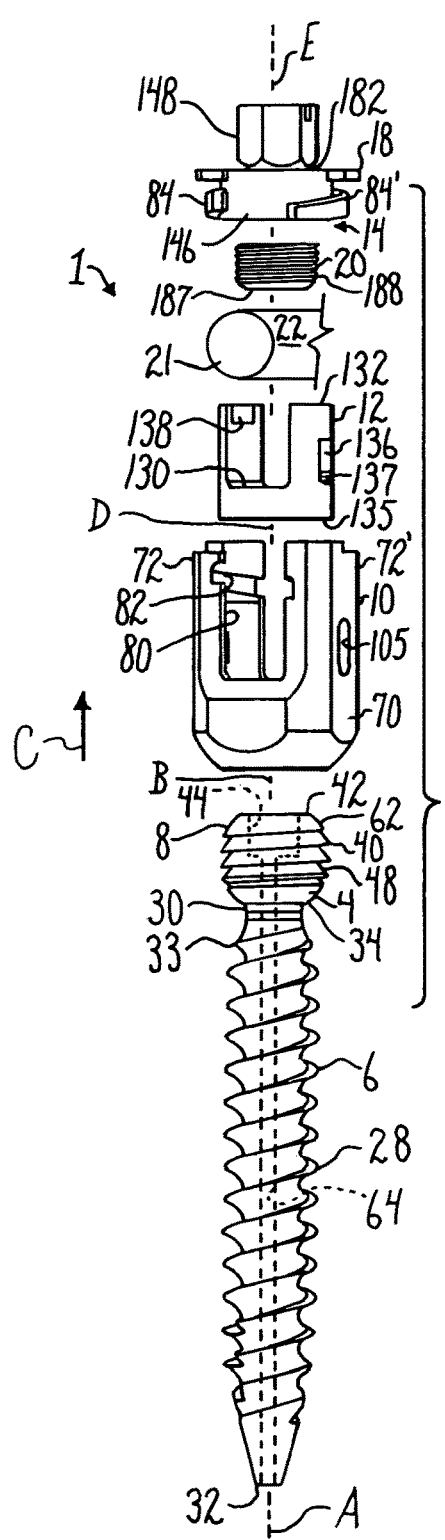
FIG. 1 is an enlarged, partial and exploded perspective view of a bone screw assembly according to the invention including a bone screw shank, a receiver, a lower compression insert and a closure structure having an outer fastener and an inner set screw and shown with a longitudinal connecting member in the form of a rod.
Figure 2:
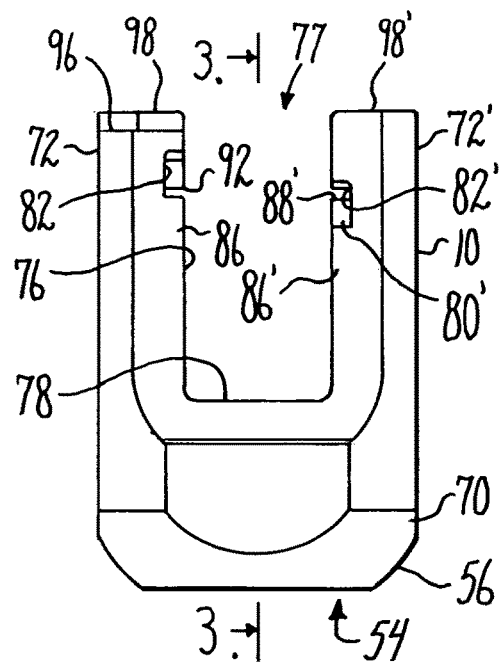
FIG. 2 is an enlarged front elevational view of the receiver of FIG. 1.
Figure 3:
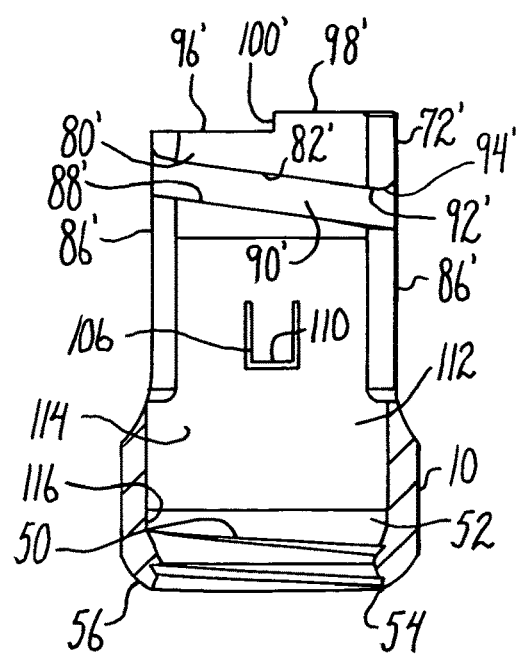
FIG. 3 is an enlarged cross-sectional view taken along the line 3-3 of FIG. 1.
Figure 12:
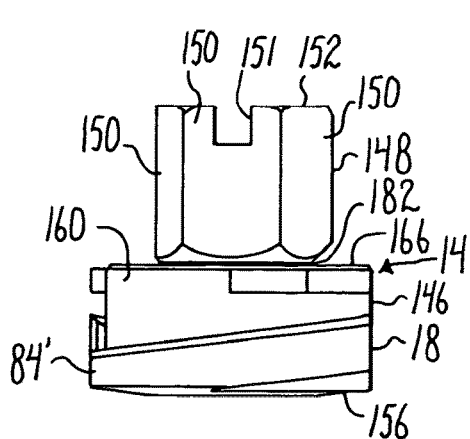
FIG. 12 is an enlarged side elevational view of the closure structure of FIG. 1.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of bone attachment assemblies of the application and cooperating connecting members in actual use.

With reference to FIGS. 1-21, the reference number 1 generally represents an embodiment of a polyaxial bone screw apparatus or assembly according to the present invention. The assembly 1 includes a shank 4 that further includes a threaded body 6 integral with an upper portion 8; a receiver 10; a lower compression insert 12; and a dual closure structure, generally 14. The shank 4, receiver 10, and compression insert 12 are typically factory assembled prior to implantation of the shank body 6 into a vertebra (not shown). However, if desirable in certain situations, the shank may be implanted into a vertebra first and thereafter the receiver threadably connected thereto.

With further reference to FIG. 1, the closure structure 14 further includes an outer fastener 18 and an inner set screw 20 for engaging a longitudinal connecting member such as a rod 21 having a cylindrical surface 22 shown in FIGS. 1 and 17-19, for example, or a longitudinal connecting member that does not have a circular cross-section, such as the bar 24 having a square or rectangular cross-section and planar surfaces 25 shown in FIGS. 20 and 21. The outer fastener 18 presses against the compression insert 12 that in turn presses upon the shank upper portion 8 which biases the portion 8 into fixed frictional contact with the receiver 10, so as to fix the rod 21 or the bar 24 relative to the vertebra (not shown). The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with respect to the shank 4 until both are locked or fixed relative to each other near the end of an implantation procedure. The rod 21 or the bar 24 may be advantageously manipulated independently of locking the shank 4 with respect to the receiver 10 and then ultimately locked into place in the receiver 10 by rotation of the set screw 20 into direct engagement with the rod 21 or bar 24. Thus, if the rod 21 or the bar 24 is made from a material such as rubber or PEEK, that exhibits any viscoelastic flow or creep, any resultant loosening of the rod 21 or the bar 24 with respect to the set screw 20 would have no impact on the security of the polyaxial locking of the shank 4 with respect to the receiver 10 provided by the pressure placed on the polyaxial mechanism by the outer fastener 18 through the insert 12.

With particular reference to FIGS. 1, 18 and 19, the shank 4 is elongate, with the shank body 6 having a helically wound bone implantable thread 28 extending from near a neck 30 located adjacent to the upper portion 8 to a tip 32 of the body 6 and extending radially outwardly therefrom. During use, the body 6 utilizing the thread 28 for gripping and advancement is implanted into the vertebra (not shown) leading with the tip 32 and driven down into the vertebra with an installation or driving tool, so as to be implanted in the vertebra to near the neck 30, and as is described more fully in the paragraphs below. The shank 4 has an elongate axis of rotation generally identified by the reference letter A.

The neck 30 extends axially upwardly from the shank body 6. The neck 30 is of slightly reduced radius as compared to an adjacent top 33 of the threaded body 6. Further extending axially upwardly from the neck 30 is the shank upper portion 8 that provides a connective or capture apparatus disposed at a distance from the threaded body top 33 and thus at a distance from the vertebra when the body 6 is implanted in the vertebra.

The shank upper portion 8 is configured for a polyaxial connection between the shank 4 and the receiver 10 and capturing the shank 4 upper portion 8 in the receiver 10. The neck 30 extends axially upwardly from the shank body 6 to a base 34 of the upper portion 8. The upper portion 8 has an outer partially spherically shaped surface 40 extending from the base 34 to a planar top portion 42. Formed in the top portion 42 is an internal drive mechanism 44 illustrated as a hex drive. The internal drive 44 is coaxial with the shank 4. The drive 44 is sized and shaped for engagement with a driving tool (not shown) that is received by the drive 44 so as to form a socket and mating projection combination for both operably driving and rotating the shank body 6 into a vertebra.

The illustrated base 34 of the portion 8 has a smooth surface, but it is foreseen that the base 34 may have a high-friction or roughened surface, such as a scored or knurled surface. Formed on the spherical surface 40 is a helical guide and advancement structure 48. The guide and advancement structure 48 retains the substantially spherical outer shape of the surface 40 at a crest thereof, but may be otherwise described as a substantially buttress thread form, sized and shaped to mate with a cooperating guide and advancement structure 50 disposed on an inner surface 52 of the receiver 10 disposed adjacent to and defining an opening 54 of a lower end or bottom 56 of the receiver 10 (see FIGS. 2 and 3). Preferably, the guide and advancement structure 48 is relatively thick and heavy to give strength to the thread and prevent the thread from being easily bent or deformed when axial pressure is applied to the shank 4 to maintain the upper portion 8 in the receiver 10. The guide and advancement structure 48 winds about the spherical surface 40 in a generally helical pattern or configuration that is typical of threads and can have various pitches, be clockwise or counterclockwise advanced, or vary in most of the ways that conventional buttress or square threads vary. The guide and advancement structure 48 has a leading surface or flank 58 and a trailing surface or flank 59. As used herein, the terms leading and trailing refer to the direction of advancement of the upper portion 8 into the guide and advancement structure 50 of the receiver 10 aligning the axis A of the shank 4 with an elongate axis of rotation B of the receiver 10 and directing the upper portion 8 toward the receiver 10, as shown by the straight arrow C illustrated in FIG. 1. Although the substantially buttress thread form 48 is described herein, it is foreseen that other thread types, such as square threads, V-threads, inverted thread types, other thread-like or non-thread-like guide and advancement structures, such as flange form helically wound advancement structures may be utilized according to the invention.

Advancement of the upper portion 8 into the receiver 10 is accomplished by rotating the shank 4 in a clockwise or counterclockwise direction about the axes A and B and into the receiver 10. A crest surface 60 connecting the leading surface 58 and the trailing surface 59 is a loading surface after the upper portion 8 is fully disposed in the receiver 10. Although discontinuous, the spherical surface 40 that includes the crest surface 60 has an outer radius that is approximately equal to a radius of an inner seating surface of the receiver 10, allowing for slidable mating contact between the surface 60 and the inner seating surface of the receiver 10.

An upper portion 62 of the spherical surface 40 located adjacent to the top planar surface 42 is advantageously substantially spherical for sliding engagement and ultimate positive frictional mating engagement with the compression insert 12, when the bone screw assembly 1 is assembled, as shown in FIG. 19 and in any alignment of the shank 4 relative to the receiver 10. In certain embodiments, the surface 62 is smooth. While not required in accordance with the practice of the invention, the surface 62 may be scored or knurled to further increase frictional positive mating engagement between the surface 62 and the compression insert 12.

The shank 4 shown in the drawings is cannulated, having a small central bore 64 extending an entire length of the shank 4 along the axis A. The bore 64 is defined by an inner cylindrical wall of the shank 4 and has a circular opening at the shank tip 32 and an upper opening communicating with the internal drive 44. The bore 64 provides a passage through the shank 4 interior for a length of wire (not shown) inserted into the vertebra (not shown) prior to the insertion of the shank body 6, the wire providing a guide for insertion of the shank body 6 into the vertebra (not shown).

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

Referring to FIGS. 1-6 and 10-11, the receiver 10 has a generally squared-off U-shaped appearance with a partially cylindrical inner profile and a substantially faceted outer profile; however, the outer profile could also be of another configuration, for example, curved or cylindrical. The receiver axis of rotation B, as shown in FIG. 1, is aligned with the axis of rotation A of the shank 4 during assembly of the receiver 10 with the shank 4 and the insert 12. After the receiver 10 is pivotally attached to the shank 4, and the assembly 1 is implanted in a vertebra (not shown), the axis B is typically disposed at an angle with respect to the axis A of the shank 4.

The receiver 10 includes a base 70 integral with a pair of opposed substantially similar or identical upstanding opposed arms 72 and 72' forming a squared-off U-shaped cradle and defining a channel 76 between the arms 72 and 72' with an upper opening 77 and a lower seat 78, the channel 76 sized and shaped for operably receiving the rod 21 or the bar 24. Each of the arms 72 and 72' has an interior surface 80 and 80', respectively, each having an inner cylindrical profile with opposed sloping interlocking flanged recesses or tracks 82 and 82' configured to mate under rotation with a pair of opposed interlocking flange forms 84 and 84' on the fastener 18, as described more fully below. Each of the tracks 82 and 82' run between and through pairs of parallel side surfaces 86 and 86' of respective arms 72 and 72'. With particular reference to FIG. 19, each track 82 and 82' is defined by a respective lower substantially planar surface 88 and 88' running about the respective cylindrical interior surface 80 and 80'; a respective outer cylindrical surface 90 and 90' running substantially parallel to the respective surfaces 80 and 80', and a respective upper flanged portion 92 and 92' also running about the respective interior surfaces 80 and 80' and having a respective surface 94 and 94' that extends downwardly (toward the base 70) and inwardly (toward the axis B) from the respective surface 90 and 90'. As best shown in FIG. 5, the tracks 82 and 82' are substantially identical in form and are located similarly on the respective arms 72 and 72' with the exception that such tracks slope in opposite directions, each having a higher end disposed near a respective planar stepped or lower top surface portion 96 and 96' of the respective arms 72 and 72' and a lower end disposed near a respective planar upper top surface 98 and 98' of the arms 72 and 72'. The respective lower surfaces 96 and 96' connected to respective upper surface 98 and 98' by respective planar walls or stops 100 and 100'. The walls or stops 100 and 100' are each disposed parallel to the axis B.

Opposed tool engaging apertures 105 are formed on or through surfaces of the arms 72 and 72' that may be used for holding the receiver 10 during assembly with the shank 4 and the retainer structure 12 and also during the implantation of the shank body 6 into a vertebra (not shown). It is foreseen that tool receiving grooves or apertures may be configured in a variety of shapes and sizes and be disposed at other locations on the receiver arms 72 and 72'. A pair of opposed spring tabs 106, each having an upper body portion integral with a respective arm 72 or 72', and a lower insert engaging surface 110 extending downwardly and inwardly from the respective upper body portion. The tabs 106 are generally directed towards the axis B and extend downwardly away from the guide tracks 82 and 82'. The lower end surfaces 110 are thus positioned to engage the compression insert 12 and hold such insert in a desired position as will be described in greater detail below. The tabs 106 are typically initially disposed parallel to the axis B and then a tool (not shown) is inserted into the aperture 105 from outside of the receiver 10 to engage and push the respective tab 106, thereby bending the tab 106 inwardly in a direction toward the axis B until the tab 106 is at a desired angular position, such as is illustrated in FIG. 5. Such bending of the tabs 106 may be performed either prior to or after assembly of the receiver 10 with the shank 4 and the compression insert 12. In the illustrated embodiment, the tabs 106 are bent inwardly prior to installation with the components 4 and 12. It is also foreseen that the tabs 106 may be machined or otherwise pre-fabricated to be angled or directed toward the axis B so as to engage the insert 12 as shown in the drawing figures. The illustrated tabs 106 are resilient, having a spring-like nature. Thus, when operatively cooperating with the insert 12, the tabs 106 bias against the insert 12, holding such insert in a desired position; and yet the tabs 106 are flexible enough to allow a user to make desired adjustments of the position of the insert 12 within the receiver 10.

With further reference to FIGS. 1-5, communicating with and located beneath the channel 76 of the receiver 10 is a chamber or cavity, generally 112, defined in part by an inner substantially cylindrical surface 114 and also the lower internal surface 52 previously described herein that includes the guide and advancement structure 50 and also includes a substantially spherical seating surface portion 116. The cylindrical surface 114 that defines a portion of the cavity 112 opens upwardly into the channel 76. The inner surface 116 that is located below the surface 114 is sized and shaped for mating with the shank upper portion 8 spherical surface 40 that includes the crest surfaces 60.

As described above, the surface portion 116 is part of the inner surface 52 that includes the opening 54. The opening 54 communicates with both the cavity 112 and the receiver lower exterior or bottom 56 of the base 70. The opening 54 is substantially coaxially aligned with respect to the rotational axis B of the receiver 10. The opening 54 is also sized and shaped to be smaller than an outer radial dimension of the shank upper portion 8 after the portion 8 has been threadably rotated through the opening 54, so as to form a restriction to prevent the portion 8 from passing through the cavity 112 and out into the lower exterior 56 of the receiver 10 during operation thereof.

With particular reference to FIGS. 1 and, 7-11 and 19, the compression insert 12 is sized and shaped to be received by and downloaded into the receiver 10 through the opening 77. In operation, a portion of the insert 12 is disposed between the rod 21 or the bar 24 and the upper portion 8 of the bone screw 4 as illustrated, for example, in FIG. 19. In operation, the closure structure 14 outer fastener 18 presses directly upon the insert 12 that in turn presses upon the shank upper portion 8, pressing the upper portion 8 against the seating surface portion 116 of the receiver 10, resulting in frictional engagement and locking of the angular position of the bone screw shank 4 with respect to the receiver 10 while allowing for further manipulation of the rod 21 or bar 24 until such rod or bar is locked into place by engagement with the inner set screw 20. The compression insert 12 has an operational central axis D that is the same as the central axis B of the receiver 10.

With particular reference to FIGS. 7-9, the compression insert 12 has a central channel or through bore substantially defined by an inner cylindrical surface 120 and an inner partially spherical surface 122, both having the central axis D. The compression insert 12 through bore is sized and shaped to receive a driving tool (not shown) therethrough that engages the shank drive feature 44 when the shank body 6 is driven into bone. The surface 122 is sized and shaped to cooperate with the spherical surface 62 of the shank upper portion 8 such that the surface 122 slidingly and pivotally mates with the spherical surface 62. The surface 122 may include a roughening or surface finish to aid in frictional contact between the surface 122 and the surface 62, once a desired angle of articulation of the shank 4 with respect to the receiver 10 is reached.

The compression insert 12 also includes a pair of arms 124 with a squared-off U-shaped surface or saddle 126 formed therebetween. The saddle 126 defines a channel that communicates with the bore defined by the cylindrical surface 120 and the spherical surface 122. The saddle 126 is substantially defined by a pair of planar opposed parallel surfaces 128 and a planar bottom or seating surface 130, the surfaces 128 and 130 being sized and shaped to closely receive the cylindrical rod 21 or the bar 24 planar surfaces 25. The saddle 126 extends from top surfaces 132 to the bottom seating surface 130. A base having an outer cylindrical surface 134 is disposed between the saddle 126 and an annular bottom surface 135. The cylindrical surface 134 also extends about the arms 124. Formed in the surface 124 and located centrally with respect to each arm 124 outer cylindrical surface is a shallow groove 136 having a substantially flat surface. In the illustrated embodiment a surface portion 137 disposed adjacent to each groove 136 and located between such groove 136 and the bottom surface 135 includes a plurality of ridges or other roughened surface features. The grooves 136 are sized and shaped to cooperate with the tabs 106 of the receiver 10 as will be described in greater detail below. The roughened surface portions 137 further cooperate with the tabs 106 to frictionally check or otherwise prohibit relative movement between the tabs 106 and such surfaces 137 during assembly and operation of the assembly 1. The grooves 136 may be of any shape, but are preferably elongate with the flat surface running parallel to the axis D and having a width that receives the respective tab 106. The illustrated bottom surface 135 is substantially planar and annular and disposed perpendicular to the axis D. Formed on the planar side surfaces 128 and also formed into the top surface 132 are a pair of opposed recesses 138, each recess having a cylindrical surface 140 running parallel to the axis D and a planar bottom surface 141 disposed perpendicular to the axis D. The recesses 138 are sized and shaped to provide clearance for the inner set screw 20 of the closure structure 14 as the set screw 20 is rotated down into engagement with the rod 21 or the bar 24 as will be described in greater detail below.

The compression or pressure insert 12 ultimately seats on the shank upper portion 8 and is disposed substantially in the upper cylindrical portion 114 of the cavity 112, with the tabs 106 engaging the insert 12 at the grooves 136, thereby holding the insert 12 in a desired alignment within the receiver 10 as will be described in greater detail below. In operation, the insert 12 extends at least partially into the receiver channel 76 such that the saddle 126 surface substantially contacts and engages the outer surface 22 of the rod 21 (or one of the planar surfaces 25 of the bar 24) when such rod or bar is placed in the receiver 10, keeping the rod or bar in spaced relation with the receiver 10 lower seating surface 78.

Figure 13:
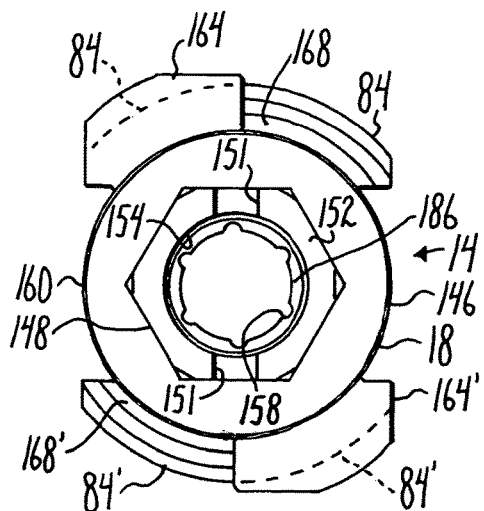
FIG. 13 is an enlarged top plan view of the closure structure of FIG. 1.

FIGS. 1 and 12-16 illustrate the nested closure structure or closure top 14 that includes the outer fastener 18 and the uploaded inner set screw 20 that are coaxial along a central axis E that in operation is the same as the axis B of the receiver 10. The fastener 18 further includes a base 146 integral or otherwise attached to a break-off head 148. The base 146 cooperates with the receiver 10 to capture the rod 21 or the bar 24 (or any other longitudinal connecting member) within the bone screw receiver 10. The break-off installation head 148 is in the form of a hex-shaped external drive feature having six planar surfaces 150 sized and shaped for engagement with a socket tool (not shown) for installing the fastener 14 to the bone screw receiver 10 and thereafter separating the break-off head 148 from the respective base 146 when installation torque exceeds selected levels. A through slot 151 formed in a top surface 152 of the break-off head 148 and disposed perpendicular to the axis E may also be utilized to manipulate and/or rotate the closure 14. A through-bore 154 extends along the axis E completely through the fastener 18 from the top surface 152 of the break-off head 148 to a bottom surface 156 of the base 146. As illustrated in FIG. 13, the portion of the bore 154 running through the break-off head 148 is sized and shaped to receive and provide some clearance around a tool (not shown) engaging an inner drive 158 of the inner set screw 20.

The base 146 of the fastener 18 is substantially cylindrical, having an external surface 160. The flange forms 84 and 84' project substantially radially and oppositely from the surface 160 near the bottom surface 156. A pair of opposed substantially flat wing members 164 and 164' also extend radially from the surface 160 and are located near a top surface 166 of the base 146. The flanges 84 and 84' are sized and shaped to slidingly mate with respective lower surfaces 88 and 88', cylindrical surfaces 90 and 90' and flanged portions 92 and 92' of the respective tracks 82 and 82' of the receiver 10. Inwardly facing surfaces 168 and 168' of the respective flanges 84 and 84' slidingly cooperate and engage the flanged portions 92 and 92', respectively, to provide an interlocking relationship between the fastener 18 and the receiver arms 72 and 72' and are thus splay resistant and do not exert radially outward forces on the arms of the receiver 10, thereby avoiding tendencies toward splaying of the receiver arms when the fastener 18 is tightly torqued into the receiver 10. The wing members 164 and 164' are plate-like with upper and lower parallel substantially planar surfaces. The wing members 164 and 164' are sized and shaped to slidingly mate with respective step surfaces 96 and 96' of the receiver 10 and abut against respective surfaces 100 and 100' when the flanges 84 and 84' are rotated into a final fixed frictional engagement with respective tracks 82 and 82' as illustrated, for example, in FIGS. 19 and 20.

At the fastener base 146 the bore 154 is substantially defined by a guide and advancement structure shown in the drawing figures as an internal V-shaped thread 176. The thread 176 is sized and shaped to receive the threaded set screw 20 therein as will be discussed in more detail below. Although a traditional V-shaped thread 176 is shown, it is foreseen that other types of helical guide and advancement structures may be used. Near a top of the base 146, an abutment shoulder 178, extends uniformly radially inwardly. The abutment shoulder 178 is spaced from the V-shaped thread 176 and sized and shaped to be a stop for the set screw 20, prohibiting the set screw 20 from advancing upwardly out of the base 146. It is foreseen that alternatively, the set screw may be equipped with an outwardly extending abutment feature near a base thereof, with complimentary alterations made in the fastener base 146, such that the set screw 20 would be prohibited from advancing upwardly out of the top of the base 146 due to abutment of such outwardly extending feature against a surface of the base 146.

An inner cylindrical wall 180 separates the abutment shoulder 178 from the thread 176. The cylindrical wall 180 has a diameter equal to or slightly greater than a root or major diameter of the internal thread 176. The wall 180 partially defines a cylindrical space or passage for axial adjustable placement of the screw 20 with respect to the longitudinal connecting member 21 or 24.

The fastener break-off head 148 is integral or otherwise attached to the fastener base 146 at a neck or weakened region 182. The neck 182 is dimensioned in thickness to control the torque at which the break-off head 148 separates from the fastener base 146. The preselected separation torque of the neck 182 is designed to provide secure engagement between the fastener base 146 and the lower compression insert 12 that in turn presses against the shank upper portion 8, clamping the shank 4 in a desired angular orientation with respect to the receiver 10. The fastener 18 captures the longitudinal connecting member 21 or 24 within the receiver 10 before the head 148 separates, by abutting against the lower compression insert 12 without making contact with the rod 21 or the bar 24. For example, 120 inch pounds of force may be a selected break-off torque to lock the bone screw shank in place without placing any pressure on the rod 21 or the bar 24. Separation of the break-off head 148 leaves only the more compact base 146 of the fastener 18 installed in the bone screw receiver 10, so that the installed fastener 18 has a low profile. As will be described in greater detail below, the set screw 20 may then be rotated and moved downwardly into secure engagement with the rod 21 or the bar 24. Thus, if the rod 21 or bar 24 experiences viscoelastic flow and the engagement between the screw 20 and the rod 21 or bar 24 is loosened, such loosening will not loosen frictional engagement between the fastener base 146, the insert 12, the shank upper portion 8 and the surface 116 of the receiver 10.

The uploadable set screw 20 has a substantially annular and planar top 186 and a substantially annular and planar bottom 187. The screw 20 is substantially cylindrical in shape and coaxial with the fastener 18. The screw 20 includes an outer threaded cylindrical surface 188 extending from the top 186 to the bottom surface 187. The v-shape thread of the surface 188 is sized and shaped to be received by and mated with the inner thread 176 of the fastener base 146 in a nested, coaxial relationship.

Figure 16:
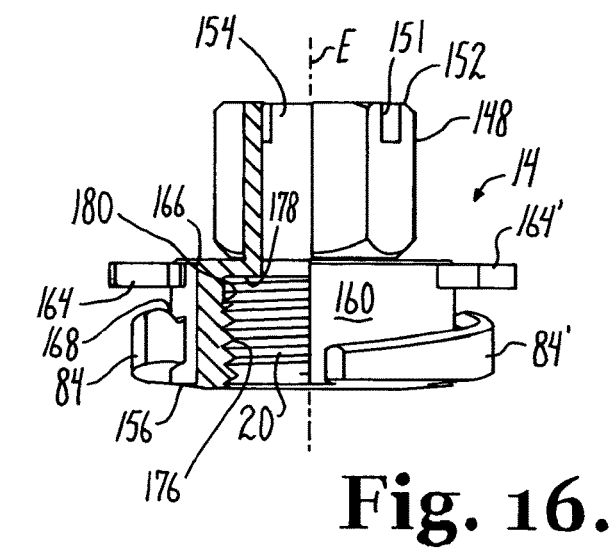
FIG. 16 is an enlarged perspective view of the closure structure of FIG. 1 with portions removed to show the detail thereof.
Figure 14:
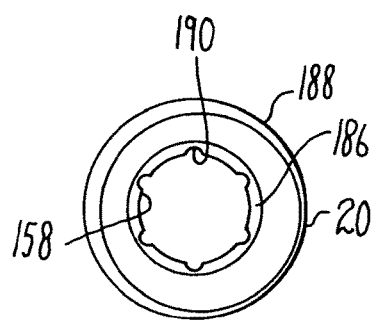
FIG. 14 is an enlarged top plan view of the set screw of the closure structure of FIG. 1.

As illustrated, for example, in FIGS. 13, 14 and 19, the set screw 20 includes a central aperture or drive 190 formed in the top 186 and sized and shaped for a positive, non-slip engagement by a set screw installment and removal tool (not shown) that may be inserted through the bore 154 of the fastener 18 and then into the drive aperture 190. With particular reference to FIGS. 16, 17 and 19, the central set screw aperture 190 cooperates with the central internal bore 154 of the fastener 18 for accessing and uploading the set screw 20 into the fastener 18 prior to engagement with the bone screw receiver 10. After the closure structure 14 is inserted and rotated into the tracks 82 and 82' of the bone screw receiver 10, and the break-off head 148 is broken off, the set screw 20 is rotated by a tool engaging the drive feature 190 to place the set screw bottom 187 into frictional engagement with the rod 21 or the bar 24. Such frictional engagement is therefore readily controllable by a surgeon so that rod 21 or the bar 24 may be readily manipulated until late in the surgery, if desired. Thus, at any desired time, the set screw 20 may be rotated to drive the screw 20 into fixed frictional engagement with the rod 21 or the bar 24 without varying the angular relationship between the receiver 10 and the bone screw shank 4.

It is foreseen that the set screw 20 may further include a cannulation through bore extending along a central axis thereof for providing a passage through the closure 14 interior for a length of wire (not shown) inserted therein to provide a guide for insertion of the closure top into the receiver arms 72 and 72'.

The elongate longitudinal connecting member that are illustrated in this application include the cylindrical rod 21 and the bar 24 of square or other rectangular cross-section. A variety of shapes are possible, including but not limited to rods or bars of oval or other curved or polygonal cross-section. Furthermore, the rod 21 or bar 24 may be a component of a dynamic stabilization connecting member, with the cylindrical or bar-shaped portions sized and shaped for being received by the insert saddle 126 also being integral or otherwise fixed to a more flexible, bendable or damping component that extends between adjacent pairs of bone screw assemblies 1. Such a rod or bar component may be made from a variety of materials including metal, metal alloys or other suitable materials, including, but not limited to plastic polymers such as polyetheretherketone (PEEK), ultra-high-molecular weight-polyethylene (UHMWP), polyurethanes and composites, including composites containing carbon fiber, as well as resorbable materials, such as polylactic acids.

With particular reference to FIGS. 1 and 17, prior to the polyaxial bone screw assembly 1 being placed in use according to the invention, the shank upper portion is pre-loaded by insertion or bottom-loading into the receiver 10 through the opening 54. The upper portion 8 is aligned with the receiver 10, with the axes A and B aligned so that the buttress thread 48 of the upper portion 8 is inserted into and rotatingly mated with the guide and advancement structure 50 on the receiver 10. The shank 4 is rotated in a clockwise or counter-clockwise direction to fully mate the structures 48 and 50, and the rotation is continued until the thread 48 disengages from the thread 50 and the upper portion 8 is fully disposed in the receiver cavity 112. The shank upper portion 8 is thus in a slidable and rotatable engagement with the receiver 10, while the upper portion 8 is maintained in the receiver 10 with the shank body 6 in pivotal or swivelable relation with the receiver 10. The shank body 6 can be pivoted or rotated through a substantial angular rotation relative to the receiver 10, both from side to side and from front to rear so as to substantially provide a universal or ball joint. The discontinuous spherical surface 40 defined by the crest surface 60 is in slidable engagement with the receiver spherical seating surface 116.

The compression or pressure insert 12 is then inserted or top loaded into the upper opening 77 of the channel 76 of the receiver 10 with the bottom surface 135 facing the top surface 42 of the shank upper portion 8 and the arms 124 aligned with the arms 72 and 72' of the receiver 10. As the insert 12 is moved downwardly toward the cavity 112, the tabs 106 are received in respective grooves 136. The tabs 106 press against the insert 12 at the grooves 136, allowing for some upward and downward adjustment of the insert 12. However, rotation of the insert 12 about the receiver axis B is prohibited by the tabs 106 abutting against cylindrical surfaces of the arms 124 and upward movement of the insert 12 out of the grip of the tabs 106 is further prohibited by the ridges of the surface portion 137. Ridges defining the surface portion 137 located at the lower curved portion of the grooves 136 also prohibit the tabs 106 from sliding along the outer cylindrical surface of the base 134, thus resisting upward movement of the insert 12 out of the receiver 10. As illustrated in FIG. 19, the insert 12 seats on the shank upper portion 8 with the surface 122 in sliding engagement with the surface 62. The bone screw is typically factory assembled with the insert 12 as shown in FIGS. 10 and 11.

In use, the bone screw with assembled insert 12 (as shown in FIGS. 10 and 11) is typically screwed into a bone, such as a vertebra (not shown), by rotation of the shank 4 using a driving tool (not shown) that operably drives and rotates the shank 4 by engagement thereof with the internal drive 44. The vertebra (not shown) may be pre-drilled to minimize stressing the bone and have a guide wire (not shown) that is shaped for the cannula 64 and inserted to provide a guide for the placement and angle of the shank 4 with respect to the vertebra. A further tap hole may be made using a tap with the guide wire as a guide. Then, the assembly 1 is threaded onto the guide wire utilizing the cannulation bore 64 by first threading the wire into the bottom opening 32 and then out of the top at the internal drive 44. The shank 4 is then driven into the vertebra, using the wire as a placement guide.

Figure 15:
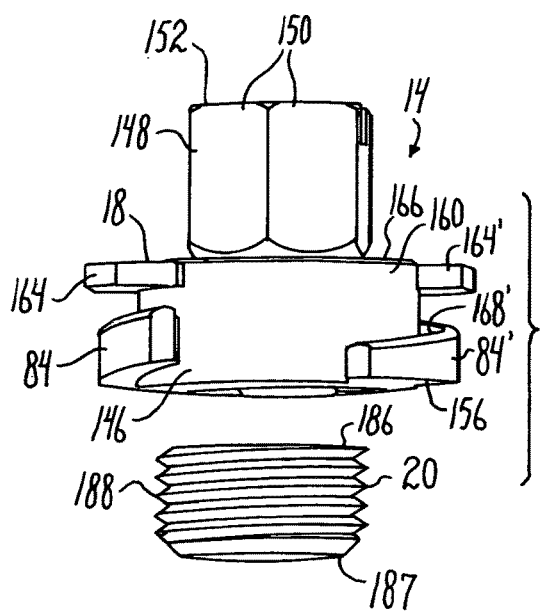
FIG. 15 is an enlarged and exploded front elevational view of the closure structure of FIG. 1.

With reference to FIGS. 15 and 16, prior to implantation of the fastener 14 into the receiver 10, the set screw 20 is inserted into the base 146 of the outer fastener 18 at the bore 154 that opens to the bottom surface 156. The screw 20 is rotated and drawn upwardly toward the top surface 166 of the base 146, mating the threaded surface 188 with the fastener inner thread 176. Initially, the screw 20 is rotated until the screw 20 is disposed entirely within the fastener 18 with the top surface 186 of the screw 20 being closely adjacent to or in contact with the abutment shoulder 178 as illustrated in FIG. 16.

With reference to FIG. 17, the rod 21 or other longitudinal connecting member, such as the bar 24 shown in FIGS. 20 and 21, is eventually positioned in an open or percutaneous manner within the receiver channel 76, and the closure structure 14 is then inserted into the receiver 10 by placing the flange forms 84 and 84' between the arms 72 and 72' followed by aligning the forms 84 and 84' with the respective tracks 82 and 82' of the receiver 10. Such alignment also aligns the opposed wing members 164 and 164' with the respective upper step surfaces 96 and 96'. With reference to FIG. 17, the closure structure is then rotated about the axis B to mate the flange forms 84 and 84' with the tracks 82 and 82'. Alignment of the rod surface 22 or the bar surfaces 25 with respect to the receiver channel 76 and the saddle 126 of the insert 14 is initially provided and then maintained by pressure placed at the insert grooves 136 by the tabs 106. The closure fastener 14 is rotated, using a tool engaged with the break-off head 148 hex drive 150 until a selected pressure is reached at which point the head 148 separates from the fastener base 146. Also with reference to FIG. 17, at this time, the set screw 20 is still entirely disposed within the base 146 and does not engage the rod 21 or the bar 24. However, the outer fastener 18 is in engagement with the insert 12 at the top surface 132 of the arms 124, placing the insert 12 surface 122 into frictional engagement with the surface 62 of the shank upper portion 8 that in turn places the upper portion 8 into frictional engagement with the surface 116 of the receiver 10, locking the shank 4 with respect to the receiver 10 in a desired angle with respect thereto. For example, about 80 to about 120 inch pounds pressure may be required for removing the break-off head 148 and fixing the bone screw shank 4 with respect to the receiver 10.

With reference to FIG. 19, the rod 21 (or bar 24) is eventually locked into place by utilizing a tool (not shown) inserted into the bore 154 and into engagement with the set screw inner drive 158. The tool is used to rotate the set screw 20 and drive the screw 20 downwardly until the surface 187 is in frictional engagement with the rod 21 surface 22 (or the bar 24 surface 25). With reference to FIGS. 17 and 19, as the screw 20 advances downwardly toward the rod surface 22, the screw 20 remains in spaced relation with the insert 12 with the recessed portions 138 of the insert 12 providing clearance for such downward advancement of the screw 20. Thus, when the screw 20 is pressing firmly against the rod 21, the screw 20 does not make contact with any portion of the insert 12. Only the rod 21 (or bar 24) is pressed into frictional engagement with the seating surface 130 of the insert 12. FIGS. 20 and 21 also illustrate that the set screw 20 may be rotated and driven downwardly into contact with the bar 24 (or the rod 21), if desired, prior to final torquing of the fastener 14 and removal of the break-off head 148.

As discussed above, if the frictional engagement between the set screw 20 and the rod 21 (or the bar 24) eventually loosens due to creep or other viscoelastic flow of the rod 21 (or bar 24), such loosening will not in turn loosen the lock between the receiver 10 and the bone screw shank 4. Therefore, the dual closure 14 advantageously allows for the use with a variety of longitudinal members made from a wide range of materials. As illustrated in FIGS. 20 and 21, the assembly 1 advantageously cooperates with both cylindrical rods and with bars of square or rectangular cross-section, such as the bar 24 of substantially square cross-section. The bar 24 made from PEEK, for example, provides for some dynamic, flexible support and yet due to the geometry thereof provides greater support with respect to torsional forces, for example, than would a cylindrical PEEK rod. However, whether greater or lesser stability is required, the squared-off channel provided by the insert 12 allows for the easy substitution of connecting members of round, square, rectangular or other cross-sectional shape.

It is noted that in certain embodiments according to the invention, a second pressure insert may be located between the set screw 20 and the rod 21 or bar 24. Furthermore, the rod 21 or the bar 24 may include a central through bore or lumen (not shown) allowing for threading of such rod or bar and implantation in a percutaneous or less invasive procedure.

If removal of the rod 21 or bar 24 from any of the bone screw assemblies 1 is necessary, or if it is desired to release the rod 21 or bar 24 at a particular location, such is accomplished by using the driving tool (not shown) that mates with the internal drive 158 on the set screw 20 to rotate and first loosen the rod 21 or bar 24 from the receiver 10. Continued rotation of the set screw 20 causes the set screw 20 to contact the abutment shoulder 178 and thereafter further rotation causes the outer fastener 18 to disengage from the flange tracks 82 and 82' of the receiver 10, thus removing the entire closure structure 14 from the cooperating receiver 10. Disassembly is then accomplished in reverse order to the procedure described previously herein for assembly.

With reference to FIGS. 22-40, the reference numeral 201 generally designates an alternative polyaxial bone screw assembly according to the invention for use with the rod 21 or the bar 24 previously described herein with respect to the assembly 1 and also with a variety of rigid or dynamic stabilization longitudinal connecting member assemblies. The bone screw assembly 201 is substantially similar to the bone screw assembly 401 disclosed in Applicant's US Patent Publication No. 2007/0055244, published Mar. 8, 2007 (U.S. patent application Ser. No. 11/522,503 filed Sep. 14, 2006) and incorporated by reference herein (hereafter the '244 publication) and illustrated in FIGS. 22-34 therein. There are a few exceptions, however, including a preferred polyaxial bone screw shank and retainer connection that allows for the lower pressure insert to exclusively directly frictionally engage the bone screw shank rather than pressing upon the retainer that is threadably attached to the shank and configured for polyaxial motion with respect to the receiver; the addition of receiver spring tabs for holding the lower pressure insert in alignment; and squared-off channels formed by the receiver and the lower pressure insert for closely receiving connecting members of rectangular cross-section as well as cylindrical members, all of which will be described in greater detail in the following paragraphs.

The bone screw assembly 201 of the present invention includes a shank 204 that further includes a body 206 integral with an upwardly extending, substantially cylindrical upper portion or capture structure 208 operationally disposed primarily within a receiver 210. The shank 204 is similar to the shank 414 disclosed in the '244 publication in that the body 206 includes a helical thread 211 for attachment to a vertebrae. The assembly 201 further includes a retainer in the form of a retaining and articulating structure 212 that is similar but not identical to the retainer disclosed in the '244 publication. The shank upper portion 208 also includes a substantially spherically shaped upper or top surface 213 sized and shaped to slidingly mate with a lower spherical surface of a lower pressure insert 214. Therefore, unlike the bone screw disclosed in the '244 publication, the pressure insert 214 operationally presses directly against the shank upper portion 208 and not the retainer 212. The shank 204, the receiver 210, the retaining and articulating structure 212 and the first or lower compression insert 214 are preferably assembled prior to implantation of the shank body 206 into a vertebra. The shank body may include a cannulation bore 264 similar in form and function to the bore 64 of the shank 4 of the assembly 1.

With particular reference to FIGS. 22 and 31-35, the shank upper portion 208 further includes a substantially cylindrical portion 215 having a helical thread 216 thereon, the portion 215 disposed adjacent to the spherical surface 213 and extending along an axial length thereof. The threaded cylindrical portion 215 flares or widens outwardly near an end 217 thereof into a portion 218 of slightly greater diameter than a remainder of the cylindrical portion 215. The thread 216 or other helically wound guide and advancement structure is sized and shaped to mate with an inner portion 220 of the retainer 212 having a thread 221 or other helically wound guide and advancement structure. The upper portion 208 further includes a top surface 222 having an internal drive 223 formed therein for engaging with a driving tool (not shown) for rotating the shank 204 and driving the shank 204 into a vertebra (not shown). When the retainer 212 is mated with the shank upper portion 208, an outer substantially spherical surface 224 of the retainer 212 is in sliding engagement with an inner substantially spherical seating surface 228 of the receiver 210 as described previously herein with respect to the upper portion 8 and the seating surface 116 of the assembly 1. The retainer 212 further includes a sloped or frusto-conical top surface 225 located between the inner threaded surface 220 and the outer spherical surface 224. In some embodiments of the invention the top surface 225 may be planar. With particular reference to FIG. 35, the sloped surface 225 advantageously provides for additional clearance between the retainer 212 and the lower pressure insert 214, ensuring that the insert 214 engages only the bone screw shank at the surface 213 and not any portion of the retainer 212.

With particular reference to FIGS. 23-30, the assembly 201 further includes an upper insert 226 and a closure structure, generally 230, having an outer fastener 232 and an uploaded inner set screw 234. The outer fastener 232 includes a base 236 integral or otherwise attached to a break-off head 238. The base 236 cooperates with the receiver 210 to capture the rod 21 or the bar 24 within the bone screw receiver 210. The break-off installation head 238 includes an internal drive or aperture 240 sized and shaped for engagement with a tool (not shown) for installing the fastener 232 to the bone screw receiver 210 and thereafter separating the break-off head 238 from a respective base 236 when installation torque exceeds selected levels.

The base 236 of the fastener portion 232 is substantially cylindrical, having an axis of rotation G and an external surface 250 having a guide and advancement structure 252 disposed thereon. The guide and advancement structure 252 is matingly attachable to a guide and advancement structure 253 of the bone screw receiver 210. The cooperating guide and advancement structures 252 and 253 can be of a variety of types, including, but not limited to buttress threads, reverse angle threads, or square threads, and are preferably helically wound flange forms that interlock and are splay resistant, and thus do not exert radially outward forces on the arms of the receiver 210, thereby avoiding tendencies toward splaying of the receiver arms when the fastener portion 232 is tightly torqued into the receiver 210.

The fastener portion 232 includes an internal, centrally located bore 254. At the base 236, the bore 254 is substantially defined by a guide and advancement structure, shown in FIG. 24 as an internal V-shaped thread 256. The thread 256 is sized and shaped to receive the threaded set screw 234 therein as will be discussed in more detail below. Although a traditional V-shaped thread 256 is shown, it is foreseen that other types of helical guide and advancement structures may be used. Near a top of the base 236, an abutment shoulder 260, extends uniformly radially inwardly. The abutment shoulder 260 is spaced from the V-shaped thread 256 and sized and shaped to be a stop for the set screw 234, prohibiting the set screw 234 from advancing upwardly out of the base 236. It is foreseen that alternatively, the set screw may be equipped with an outwardly extending abutment feature near a base thereof, with complimentary alterations made in the fastener base 236, such that the set screw 234 would be prohibited from advancing upwardly out of the top of the base 236 due to abutment of such outwardly extending feature against a surface of the base 236.

An inner cylindrical wall 262 separates the abutment shoulder 260 from the thread 256. The cylindrical wall 262 has a diameter equal to or slightly greater than a root or major diameter of the internal thread 256. The wall 262 partially defines a cylindrical space or passage 264 for axial adjustable placement of the screw 234 with respect to the longitudinal connecting member 21 or 24.

The fastener break-off head 238 is integral or otherwise attached to the fastener 232 at a neck or weakened region 266. The neck 266 is dimensioned in thickness to control the torque at which the break-off head 238 separates from the fastener 232. The preselected separation torque of the neck 266 is designed to provide secure engagement between the fastener 232 and the lower compression structure or insert 214 that in turn presses directly against the shank upper portion 208 that is threadably mated to the retainer 212, pressing the retainer 212 against the receiver 210 and thus clamping the shank 204 in a desired angular orientation with respect to the receiver 210 and the rod 21 or the bar 24. The fastener 232 thus captures the longitudinal connecting member 21 or 24 within the receiver 210 before the head 238 separates, by abutting against the lower compression member 214 without making contact with the rod 21 or the bar 24. For example, 120 inch pounds of force may be a selected break-off torque to lock the bone screw shank in place without placing any pressure on the rod 21 or the bar 24. The illustrated internal driving feature 240 of the break-off head 238 enables positive, non-slip engagement of the head 238 by an installation and torquing tool. Separation of the break-off head 238 leaves only the more compact base 236 of the fastener 232 installed in the bone screw receiver 210, so that the installed fastener 232 has a low profile. As will be described in greater detail below, the set screw 234 may then be rotated and moved downwardly into secure engagement with the rod 21 or the bar 24.

The base 236 of the fastener 232 includes a planar bottom surface 268 disposed substantially perpendicular to the axis G for abutting the top surfaces 269 of arms of the compression insert 214. However, the bottom surface may also be ramped or inclined as described in the '244 publication (with cooperating ramped surface on the insert 214).

The uploadable set screw 234 has a substantially annular and planar top 276 and a substantially annular and planar bottom 277. The screw 234 is substantially cylindrical in shape and coaxial with the fastener 232. The screw 234 includes an outer cylindrical surface 278 disposed near the bottom 277 and a threaded surface 280 extending from the top 276 to the cylindrical surface 278. The v-shaped thread 280 is sized and shaped to be received by and mated with the inner thread 256 of the fastener base 236 in a nested, coaxial relationship.

As illustrated, for example, in FIGS. 24 and 25, the set screw 234 includes a central aperture 286 formed in the top 276 and defined by side walls 288 that define a driving feature similar to but of smaller dimensions than the driving feature 240 of the fastener 232. The driving feature further includes a seating surface or bottom 289, aiding in a positive, non-slip engagement by a set screw installment and removal tool (not shown) that may be inserted through the aperture formed by the driving feature 240 of the fastener 232 and then into the aperture 286 and into engagement with the walls 288 defining the set screw driving feature. A lower central aperture or bore 290 extends between the central aperture 286 and the bottom 277 of the set screw 234. The bore 290 is sized and shaped to receive and hold an upper portion of the upper compression structure 226 as will be described more fully below.

With further reference to FIG. 24, the central set screw aperture 286 cooperates with the central internal bore 254 of the fastener 232 for accessing and uploading the set screw 234 into the fastener 232 prior to engagement with the bone screw receiver 220. After the closure structure 230 is inserted and rotated in the bone screw receiver 210, and the break-off head 238 is broken off, the set screw 234 is rotated by a tool engaging the drive feature walls 288 to place the set screw bottom 277 into frictional engagement with the rod 21 or bar 24.

There are circumstances under which it is desirable or necessary to release the longitudinal connecting member 21 or 24 from the bone screw assembly 201. For example, it might be necessary for a surgeon to re-adjust components of a spinal fixation system, including the longitudinal connecting member 21 or 24, during an implant procedure, following an injury to a person with such a system implanted. In such circumstances, the tool that engages and rotates the set screw 234 at the driving feature 288 may be used to remove both the set screw 234 and attached fastener base 236 as a single unit, with the set screw 234 contacting and contained within the base 236 by the abutment shoulder 260. Thus, rotation of the set screw tool engaged with the set screw 234 backs both the set screw 234 and the fastener base 236 out of the guide and advancement structure 253 in the receiver 210, thereby releasing the longitudinal connecting member 21 or 24 for removal from the bone screw receiver 210 or repositioning of the longitudinal connecting member 21 or 24. It is foreseen that other removal structures such as side slots or other screw receiving and engagement structures may be used to engage the set screw 234 that is nested in the fastener base 236.

With particular reference to FIGS. 22 and 35-37, the lower compression insert 214 includes a substantially cylindrical body 310 integral with a pair of upstanding arms 312. The body 310 and arms 312 form a generally squared-off U-shaped, open, through-channel 314 with planar side surfaces 315 disposed perpendicular to a planar bottom seating surface 316, the channel 314 and seating surface 316 sized and shaped to receive either the rod 21 or the planar surfaces 25 of the bar 24. In the illustrated embodiment, the channel surfaces 315 do not closely receive the rod 21 and as will be described below, the rod 21 is held substantially centrally in place by the upper compression insert 226. However, in other embodiments according to the invention, the lower insert may be sized and shaped to closely receive the rod 21 as well as the bar 24 as shown in FIG. 34. The arms 312 of the inert 214 disposed on either side of the channel 314 each include a top flanged portion 318, each portion 318 including the planar top surface 269 previously described herein, sized and shaped to engage the surface 268 of the fastener 232. The compression insert 214 further includes a bottom surface 320 and a substantially cylindrical outer surface 322. An inner cylindrical wall 324 defining a central through-bore extends along a central axis of the compression structure 214 and extends between the seating surface 316 and a substantially spherical surface 326. The surface 326 extends between the inner cylindrical wall 324 and the bottom surface 320. The surface 326 is substantially similar to the spherical surface 122 of the compression insert 12 previously described herein, the surface 326 being sized and shaped to frictionally engage and mate with the upper spherical surface 213 of the shank upper portion 208.

The cylindrical surface 322 has an outer diameter slightly smaller than a diameter between crests of the guide and advancement structure 253 of the receiver 210 allowing for top loading of the compression insert 214. During top load installation, the top surface portions 318 disposed on each of the upstanding arms 312 are inserted into the channel between the receiver 210 upstanding arms and then the insert 214 is rotated about the axis F with the portion 318 sized and shaped to be received into a run-out or recess located beneath the guide and advancement structure 253. The receiver 210 fully receives the lower compression insert 214 and blocks the insert 214 from spreading or splaying in any direction. It is noted that assembly of the shank 204 and the retainer 212 within the receiver 210, followed by insertion of the lower compression insert 214 into the receiver 210 are assembly steps typically performed at the factory, advantageously providing a surgeon with a polyaxial bone screw with the lower insert firmly snapped into place and thus ready for insertion into a vertebra. The through-channel 314 is sized and shaped such that the upper compression structure or insert 226 is receivable in the channel 314 between opposed upper substantially planar walls 315 that define the channel 314 from the base 316 to the top surfaces 269. Adequate clearance is provided such that the upper compression insert 226 is in slightly spaced or in sliding relationship with the walls 315, allowing for independent movement of the upper compression insert 226 with respect to the lower compression insert 214.

The lower insert 214 further includes opposed grooves 328 formed on outer surfaces of the arms 312. The grooves 328 are substantially similar in form and function to the grooves 136 of the insert 12 of the assembly 1. The grooves 328 are sized and shaped to receive spring tabs 329 of the receiver 210. The spring tabs 329 are similar in form and function to the tabs 106 previously described herein with respect to the receiver 10 of the assembly 1 with the exception that the spring tabs 329 extend from a lower portion of the receiver 210 in a direction upwardly toward the guide and advancement structure 253 as well as inwardly toward the axis F of the receiver 210.

Figure 40:
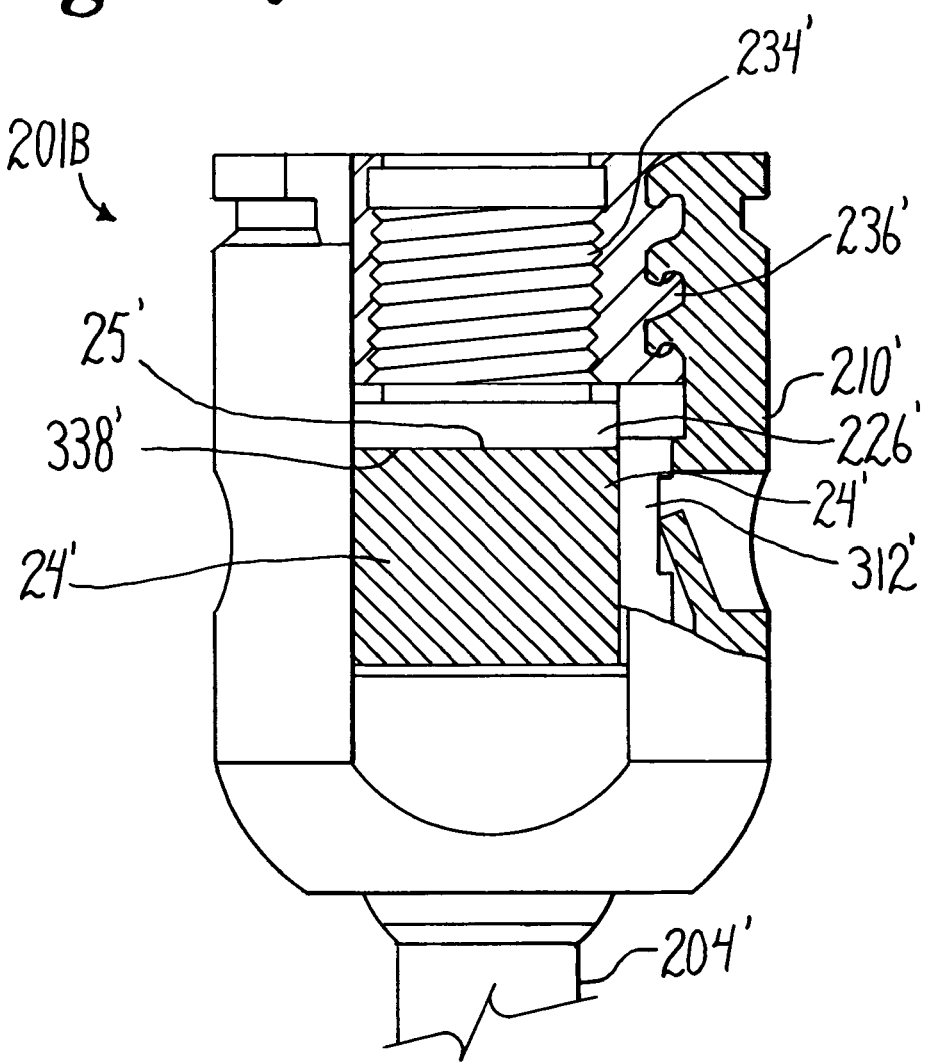
FIG. 40 is an enlarged and partial front elevational view of another embodiment according to the invention, similar to the assembly of FIG. 22, but with a different compression insert, shown assembled with the break-off top removed, with portions broken away to show the detail thereof and further showing the assembly cooperating with a longitudinal connecting member in the form of a bar of rectangular cross-section.

With reference to FIGS. 26-30, the upper or second compression structure or insert 226 includes a body 330 having a pair of downwardly extending legs 332. The body 330 and the legs 332 form a generally U-shaped, open, through-channel having a substantially U-shaped seating surface 336 having a radius substantially conforming to the outer radius of the rod 21 and thus configured to operably snugly engage the rod 21 at the external surface 22 thereof opposite the seating surface 316 of the lower compression insert 214. FIG. 40 illustrates an alternative embodiment wherein an upper insert 226' includes a planar bottom surface 338' for engaging a planar top surface 25' of a bar 24'. It is further noted that the polyaxial bone screw shank 204 and cooperating threaded retainer 212 capture connection provided in the assembly 201 may also be used without an upper pressure insert and in combination with the dual closure structure 14 of the assembly 1, or alternatively, with a one-piece closure assembly.

Returning to the insert 226 of the assembly 201, the legs 332 each include a bottom surface 338 that is substantially parallel to a planar top surface 340. The compression insert 226 includes a pair of opposed curved outer surfaces 342 substantially perpendicular to the top surface 340 and extending between the top surface 340 and the seating surface 336. The curved surfaces 342 further extend along the legs 332 and terminate at the bottom surfaces 338. A pair of opposed substantially planar outer surfaces 343 are disposed between the curved surfaces 342 and are also disposed substantially perpendicular to the top surface 340, each planar surface 343 extending between the top surface 340 and a respective bottom surface 338.

A pin 344 of substantially circular cross section is disposed centrally on the top surface 340 and extends upwardly therefrom, being sized and shaped to fit within the centrally located lower bore 290 formed in the set screw 234. The pin 344 further includes a substantially cylindrical base 346 and a U-shaped channel 348 formed by a pair of opposed, flanged arms 350 that extend from the base 346 upwardly and substantially parallel to one another. Each of the flanged arms includes a partially conical surface portion 351 and a flat bottom surface 352 that is substantially parallel to the top planar surface 340 of the compression structure body 330. As illustrated in FIGS. 29 and 30, the pin 344 is receivable in the bore 240 with surfaces forming the bore pressing and deforming the flanged arms 350 toward one another as the upper compression structure 226 is pressed against the set screw 234 that has already been up-loaded into a fastener portion 232. Once the conical surface portions 351 clear the bore 240 and enter the set screw aperture 286, the flanged arms 350 return to the original upright and substantially parallel form with the surfaces 352 being in contact with and seated upon a portion of the bottom surface 289 as illustrated in FIG. 30. The flanged arms 350 thus keep the compression structure 226 attached to the set screw 234 and yet rotatable with respect thereto about an axis of rotation H of the cylindrical base 346 of the structure that is coaxial with the axis G of the set screw 234 and fastener 232, providing a centered relationship between the closure structure 230 and the compression structure 226 while allowing the compression structure 226 to freely rotate into a position centered over and in gripping engagement with the longitudinal connecting member 21 when assembled thereon. Furthermore, if removal of the fastener and uploaded set screw is desired, the attached compression structure 226 is advantageously removed along therewith.

With particular reference to FIGS. 24, 29, 30 and 36-38, in use, the set screw 234 is assembled with the fastener 232 by inserting a set screw tool (not shown) through the bore 254 of the fastener 232 and into the aperture 286 of the set screw 234, with outer features of the tool engaging the inner walls 288 of the set screw 234. The set screw 234 is then uploaded into the fastener 232 by rotation of the set screw 234 with respect to the fastener 232 to mate the set screw thread 280 with the fastener inner thread 256 until the set screw top surface 276 is spaced from the abutment shoulder 260, but substantially nested in the fastener 232, with possibly only the cylindrical surface 278 extending from the fastener base 236. The upper compression structure 224 is then attached to the set screw 234 as previously described with the pin 344 being received by the bore 290 and inserted therethrough until the arms 350 are disposed within the aperture 286, with the lower surfaces 352 of the flanged arms seated on the bottom 289 of the set screw aperture 286, capturing the flanged arms 350 within the aperture 286. The nested assembly shown in FIG. 24 and attached to an upper compression structure as shown in FIGS. 29 and 30 is now pre-assembled and ready for use with a bone screw receiver 210 and cooperating rod 21.

With particular reference to FIGS. 22 and 32-35, the retainer 212 is typically first inserted or top-loaded, into the receiver squared-off U-shaped channel and then into the receiver cavity. Then, the retainer 212 is rotated approximately 90 degrees so as to be coaxial with the receiver 210 axis F and then seated in sliding engagement with the inner seating surface of the receiver 210 as shown in FIG. 32. With reference to FIG. 33, the shank upper portion 208 is then inserted or bottom-loaded into the receiver 210. The retainer 212, now disposed in the receiver 210 is coaxially aligned with the shank 204 and the upper portion 208 is generally rotated about the axis F mating the threaded surface 215 with the threaded surface 220 of the retainer 212. Rotation continues until the retainer 212 engages the flared portion 218 and is tightened thereon, fixing the retainer 212 to the shank upper portion 208 as shown, for example, in FIG. 35. Preferably, the shank 204 and or the retainer 212 are rotated to fully mate such structures at a factory setting that includes tooling for holding and precisely rotating the shank 204 and/or the retainer 212 until locking frictional engagement therebetween is accomplished. At this time both the shank 204 and the retainer 212 are in rotatable and swivelable engagement with the receiver 210, while the shank upper portion 208 and the lower aperture or neck of the receiver 210 cooperate to maintain the shank body 206 in swivelable relation with the receiver 210. Only the retainer 212 is in slidable engagement with the receiver 210 spherical seating surface. The spherical shank upper surface 213 is in spaced relation with the receiver 210. The shank body 206 can be rotated and pivoted through a substantial angular rotation relative to the receiver 210, both from side to side and from front to rear so as to substantially provide a universal or ball joint.

With reference to FIG. 35, the insert 214 may be top loaded into the receiver 210 with the flanged portions 318 aligned in the receiver channel, each flanged portion 318 being located between a pair of opposed walls partially defining the receiver arms. The insert 214 is then moved downwardly into the receiver and past the guide and advancement structure 253. Once the flanged portions 318 are located below the guide and advancement structure 253 and adjacent the run-out relief below the structure 253, the insert 214 is rotated about the axis F of the receiver 210 as illustrated by the arrow 380 in FIG. 22. The flanged portions 318 fit within such relief. Once each flanged portion 318 is located centrally with a respective arm of the receiver 210, rotation is ceased and the spring tabs 329 may be pressed into the grooves 328 or the spring tabs 329 simply snap into the grooves 328 as in the illustrated embodiment of the receiver 210 wherein the tabs are directed inwardly toward the axis F prior to assembly with the lower pressure insert 214. The insert 214 is now locked into place inside the receiver 210 with the guide and advancement structure 253 prohibiting upward movement of the insert out of the receiver 210 and the spring tabs 329 that are biasing against the insert 214 at the grooves 328 prohibiting rotational movement of the insert 214 with respect to the receiver 210 about the receiver axis F. The insert 214 seats on the shank upper portion 208 with the partially spherical surface 326 in sliding engagement with the cooperating partially spherical surface 213 as best shown in FIG. 35 (and also shown in locked mated engagement in FIG. 38). It is noted that FIG. 35 illustrates the shank 204 and attached retainer 212 swivelled at an angle with respect to the receiver 210 wherein the shank body 206 is extending forward from the plane of the drawing illustration as well as at an angle with respect to the two dimensions of the drawing figure. The run-out or relief under the guide and advancement structure 253 is sized and shaped to allow for some upward and downward movement of the insert 214 toward and away from the shank upper portion 208 such that the shank upper portion 208 is freely pivotable with respect to the receiver 210 until the closure structure fastener base 236 presses on the insert 214 that in turn presses upon the upper portion 208 into locking frictional engagement with the receiver 210. Similarly, the spring tabs 329 are sized, shaped and positioned within the grooves 328 to allow for upward and downward movement of the insert 214 and pivoting of the shank 204 prior to locking in place.

Figure 36:
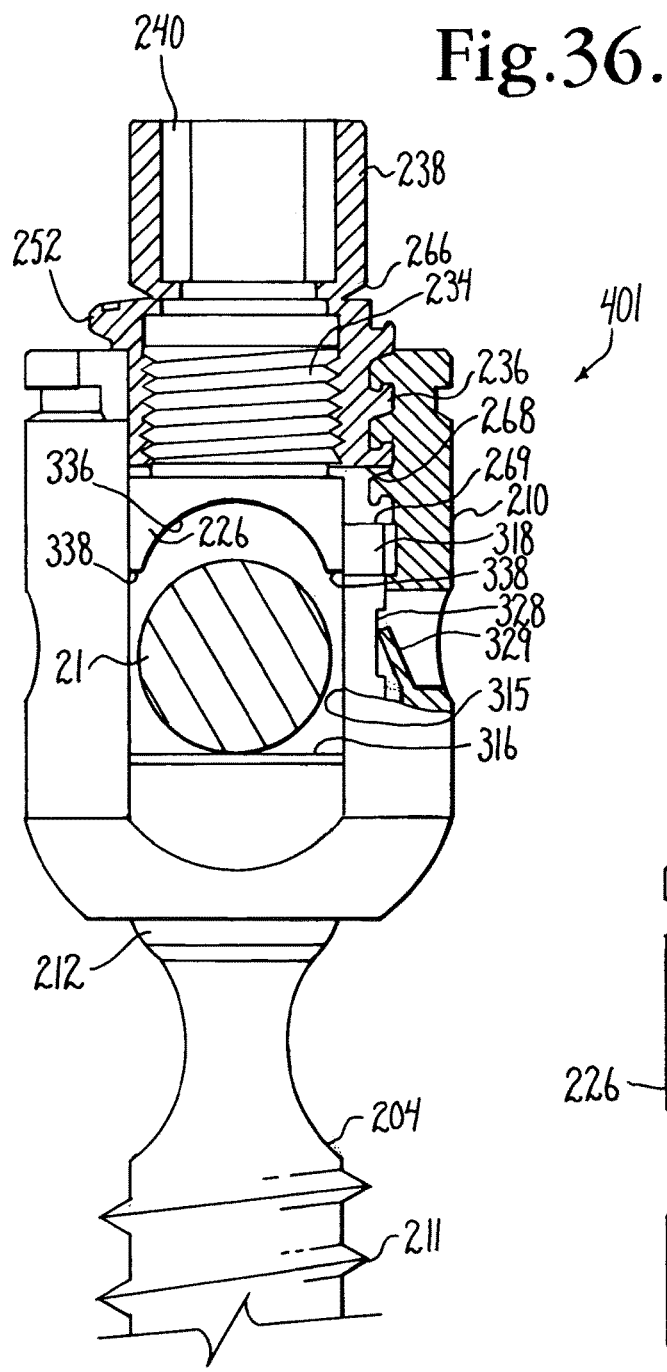
FIG. 36 is an enlarged and partial front elevational view of the assembly of FIG. 22 with portions broken away to show the detail thereof and further showing the upper compression insert and closure member partially inserted in the receiver.
Figure 37:
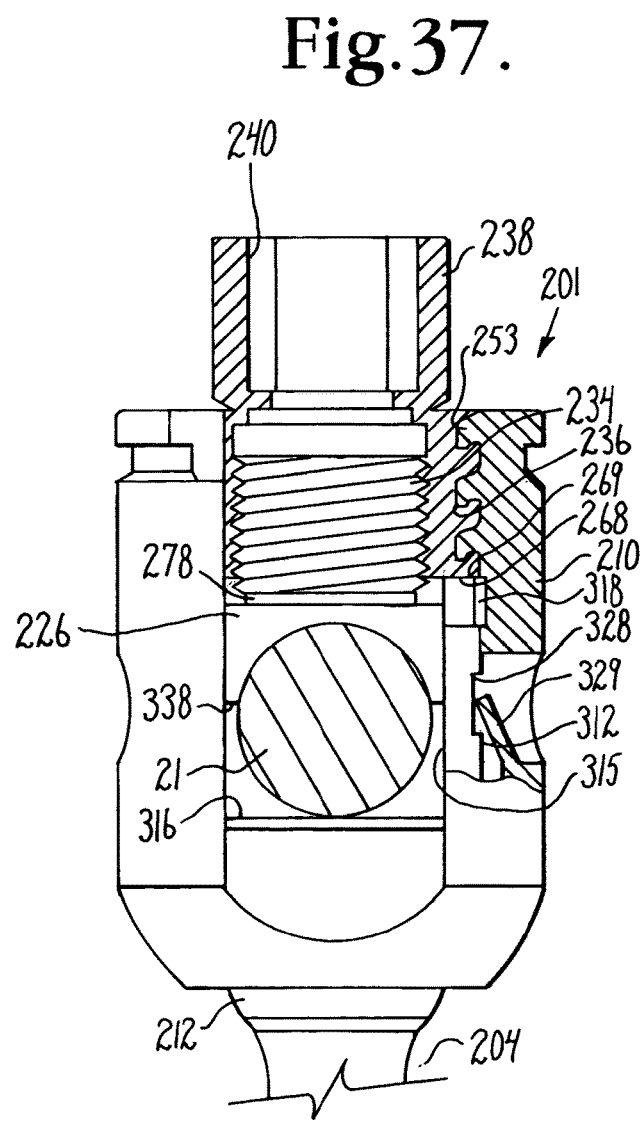
FIG. 37 is an enlarged and partial front elevational view similar to FIG. 36 showing the upper compression insert and closure member fully seated in the receiver prior to removal of the closure member break-off head.
Figure 38:
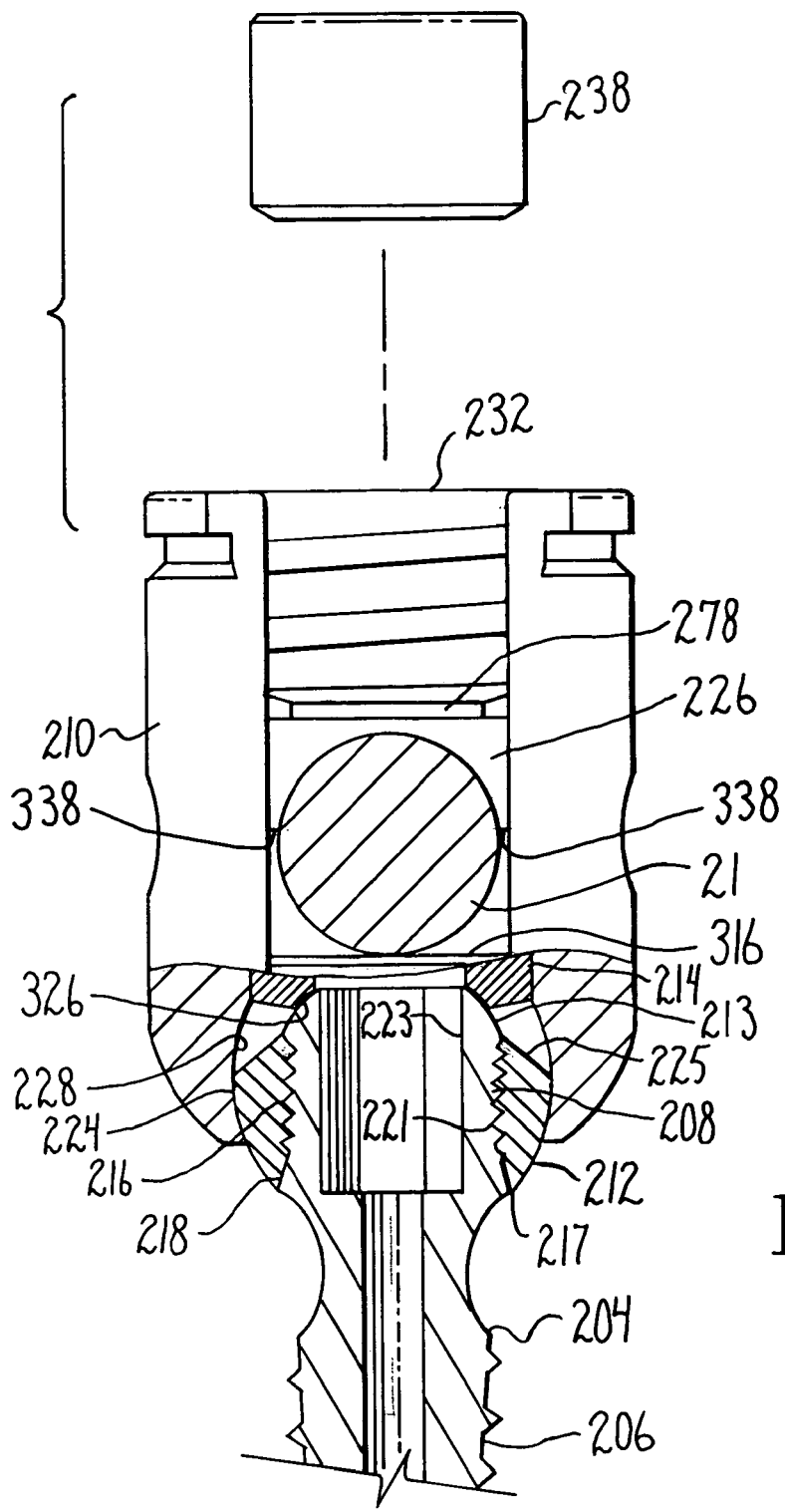
FIG. 38 is an enlarged and partial front elevational view of the assembly of FIG. 22 with portions broken away to show the detail thereof, and further showing the closure member break-off head removed.

With reference to FIG. 34, in use, the bone screw shank 206 is typically screwed into a bone, such as a vertebra 380 by rotation of the shank 204 using a driving tool 382 that operably drives and rotates the shank 204 by engagement thereof with the tool engagement structure 223. With reference to FIGS. 35-37, the rod 21 is eventually placed in the bone screw receiver 210 that has been previously attached to the bone screw shank 204 utilizing the retaining and articulating structure 212 and loaded with the lower compression insert 214. A driving tool (not shown) is used to rotate the closure structure by engagement with the drive feature 240 of the break-off head 238, mating the guide and advancement structures 252 and 253. During installation, the fastener surface 268 frictionally engages the surface 269 of the lower compression insert 214, that in turn presses the surface 326 exclusively against the shank upper portion 208 at the surface 213 at a location substantially spaced from the retainer 212 as shown in FIG. 38, biasing the retainer 212 at the surface 224 into fixed frictional contact with the receiver 210 at the seating surface 228, such that the receiver 210 and the shank 204 can be independently secured at a desired angle with respect to the receiver while the rod 21 remains movable within the receiver and yet substantially captured between the compression structures 212 and 226. Also with reference to FIG. 38, the closure structure is rotated until a selected pressure is reached at which time the head 238 breaks off, preferably about 80 to about 120 inch pounds that adequately fixes the bone screw shank 204 with respect to the receiver 210. When the break-off head is removed, the upper compression insert 226 is preferably in contact with the rod 21, but placing little if any pressure thereon. Then, a set screw driving tool (not shown) is inserted into the drive feature 288 and the set screw 234 is rotated downwardly, pressing against the insert 226 that in turn presses against the rod 21.

Figure 39:
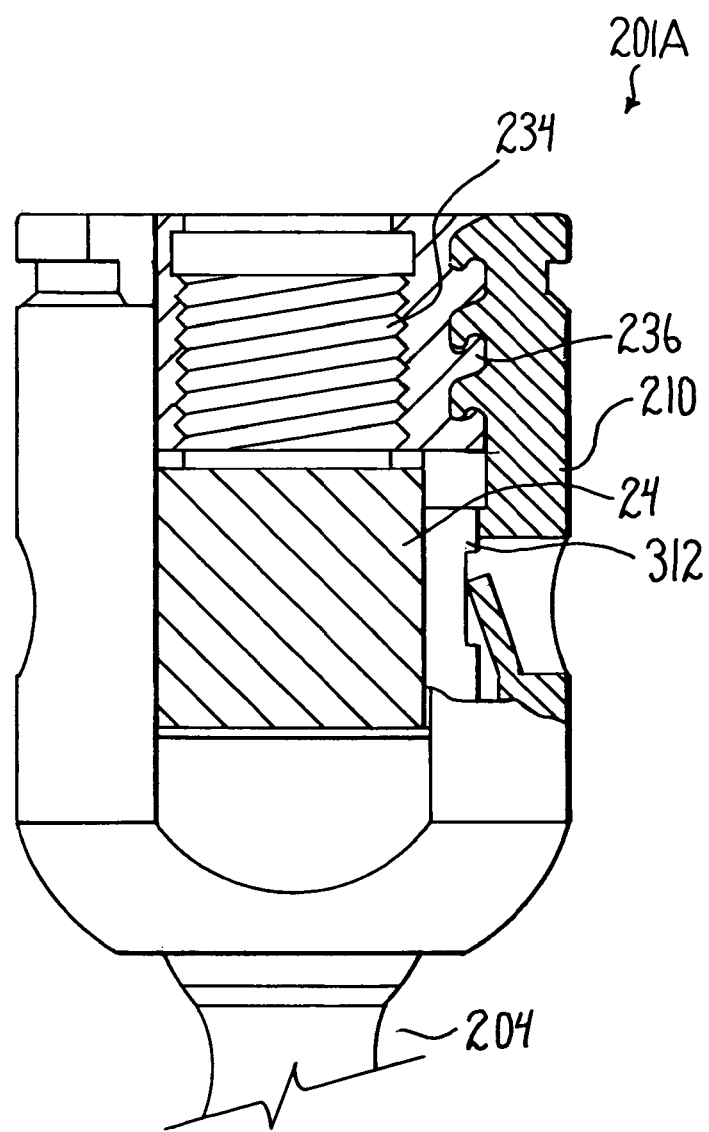
FIG. 39 is an enlarged and partial front elevational view of an alternative embodiment according to the invention, similar to the assembly of FIG. 22, but without the upper compression insert, shown assembled, with break-off top removed and with portions broken away to show the detail thereof and further showing the assembly cooperating with a longitudinal connecting member in the form of a bar of rectangular cross-section in lieu of the rod shown in FIG. 22.

The polyaxial bone screw assembly 201 according to the invention advantageously allows for the removal and replacement of the rod 21 with another longitudinal connecting member having a different overall cross-sectional width or outer diameter, utilizing the same receiver 210 and the same lower compression insert 214. For example, as illustrated in FIG. 39, an assembly 201A is illustrated wherein the rod 21 is replaced by the bar 24 and the upper insert 226 is not utilized.

With reference to FIG. 40, another assembly according the invention, generally 201B, includes a shank 204', a receiver 210', a set screw 234' and cooperating outer fastener 236', and a lower insert 312' substantially similar to the respective shank 204, receiver 210, set screw 234 and fastener 236, and insert 312 previously described herein with respect to the assembly 201. It is noted that the neck of the shank 204' is substantially cylindrical as compared to the curved neck of the shank 204. Shanks according to the invention may include a variety of geometries including, but not limited to straight cylinders, curved necks, conical necks, and the like.

The assembly 201B further includes an upper insert 226' that attaches to the set screw 234' in a manner similar to the previously described cooperation between the set screw 234 and insert 226. However, the insert 226' includes a planar bottom surface 338' for substantially full frictional contact with a planar surface 25' of a bar 24' of rectangular cross-section.

It is to be understood that while certain forms of the present invention have been illustrated and described herein, it is not to be limited to the specific forms or arrangement of parts described and shown.

What is claimed is:

1. A pivotable bone anchor assembly for securing an elongate rod to a bone of a patient via a closure top, the pivotable bone anchor assembly comprising:
   a receiver comprising a base portion defining an internal cavity in communication with a bottom surface of the receiver through a bottom opening, and an upper portion defining a channel communicating with the internal cavity and configured to receive the elongate rod, the upper portion having a mating structure formed therein configured to mate with the closure top, the internal cavity having a curved seating surface adjacent the bottom opening and the bottom opening having a first thread formed therein;
   an anchor member comprising a longitudinal axis, a proximal end portion having an internal drive socket formed therein, and an anchor portion opposite the proximal end portion configured for fixation to the bone, the proximal end portion including a lower outer curved contact surface complementary with the curved seating surface of the internal cavity, a second thread formed above the lower outer curved contact surface and threadably mateable with the first thread, and a planar top surface perpendicular to the longitudinal axis and entirely surrounding the internal drive socket, the proximal end portion of the anchor member being configured for positioning within the internal cavity of the receiver with the anchor member extending downward through the bottom opening and with the lower outer curved contact surface below the second thread in slidable engagement with the curved seating surface so as to establish pivotable motion between the anchor member and the receiver in an unlocked configuration; and an insert at least partially positionable within the channel of the receiver and having an upper surface configured to receive the elongate rod and a lower surface configured to engage the proximal end portion of the anchor member so as to direct a downwardly-directed force from the elongate rod to the proximal end portion to lock a position of the anchor member relative to the receiver in a locked configuration, wherein the planar top surface on the proximal end portion is configured to remain spaced apart from the lower surface of the insert so as to not directly receive the downwardly-directed force therefrom in the locked configuration.

2. The pivotable bone anchor assembly of claim 1, wherein the proximal end portion of the anchor member is threadably uploadable into the internal cavity through the bottom opening of the receiver until the second thread passes through the first thread and the lower outer curved contact surface becomes slidably engaged with the curved seating surface to establish the pivotable motion between the anchor member and the receiver.

3. The pivotable bone anchor assembly of claim 1, wherein the anchor member includes a central bore centered about the longitudinal axis and extending distally from the internal drive socket to a distal tip of the anchor member.

4. The pivotable bone anchor assembly of claim 1, wherein the planar top surface of the proximal end portion of the anchor member is an annular surface perpendicular to the longitudinal axis of the anchor member.

5. The pivotable bone anchor assembly of claim 1, wherein the lower outer curved contact surface of the proximal end portion of the anchor member further comprises a partially spherical-shaped surface.

6. The pivotable bone anchor assembly of claim 1, wherein the curved seating surface of the internal cavity of the receiver further comprises a partially spherical-shaped surface.

7. The pivotable bone anchor assembly of claim 1, wherein the anchor member further comprises a neck between the proximal end portion and the anchor portion, the neck having a reduced radius that is less than a radius of an immediately adjacent portion of the anchor portion and being defined by at least one smooth curvate surface extending inwardly toward the longitudinal axis of the anchor member.

8. The pivotable bone anchor assembly of claim 1, wherein the insert includes a central through-bore sized and shaped to provide passage for a driving tool configured to engage the internal drive socket of the anchor member to drive the anchor member into the bone.

9. The pivotable bone anchor assembly of claim 1, wherein the lower surface of the insert further comprises a downwardly-opening concave curved engagement surface that is complementary with an upper outer curved contact surface located at an upper end of the proximal end portion of the anchor member above the second thread.

10. The pivotable bone anchor assembly of claim 9, wherein the concave curved engagement surface of the insert is a partially spherical-shaped surface.

11. The pivotable bone anchor assembly of claim 9, wherein the upper outer curved contact surface is a partially spherical-shaped surface.

12. The pivotable bone anchor assembly of claim 9, wherein the upper outer curved contact surface is between the second thread and the planar top surface.

13. The pivotable bone anchor assembly of claim 1,
wherein the insert further comprises a base portion and a pair of insert arms extending upward from the base portion, and
wherein the upper surface of the insert further comprises an open channel defined by the pair of insert arms and configured to receive the elongate rod.

14. The pivotable bone anchor assembly of claim 1, wherein the insert is configured to be top loaded into the receiver.

15. The pivotable bone anchor assembly of claim 1, wherein the insert is configured to be positioned within the receiver prior to the anchor member.

16. The pivotable bone anchor assembly of claim 1 and further comprising the elongate rod and the closure top, wherein the closure top is configured for positioning entirely within the upper portion of the receiver above the elongate rod and in engagement with the mating structure thereof to apply a downward pressure to a top of the elongate rod, so as to secure the elongate rod to the bone of the patient in the locked configuration.

17. A pivotable bone anchor assembly for securing an elongate rod to a bone of a patient via a closure top, the pivotable bone anchor assembly comprising:
a receiver comprising a base and a pair of upright arms extending upward from the base with opposed interior surfaces forming an open channel for receiving the elongate rod and having a closure top mating structure formed therein, the base defining an internal cavity in communication with the open channel and with a bottom surface of the receiver through the bottom opening, the internal cavity having an inner seating surface adjacent the bottom opening and a first thread formed in the bottom opening and extending upward into the inner seating surface;
an anchor member comprising a longitudinal axis, a proximal end portion having an internal drive socket formed therein, and an anchor portion opposite the proximal end portion configured for fixation to the bone, the proximal end portion including a planar upper surface, a second thread formed below the planar upper surface, and a lower outer curved contact surface below the second thread; and
an insert configured to be at least partially positioned within the open channel and having an upper surface configured to receive the elongate rod and a lower surface configured to engage the proximal end portion of the anchor member,
wherein the proximal end portion of the anchor member is configured to be positioned within the internal cavity of the receiver with the planar upper surface under the lower surface of the insert and the lower outer curved contact surface in slidable engagement with the inner seating surface of the internal cavity so as to establish pivotable motion between the anchor member and the receiver.

18. The pivotable bone anchor assembly of claim 17, wherein the proximal end portion of the anchor member is threadably uploadable into the internal cavity through the bottom opening of the receiver until the second thread passes through the first thread and the lower outer curved contact surface becomes slidably engaged with the curved seating surface to establish the pivotable motion between the anchor member and the receiver.

19. The pivotable bone anchor assembly of claim 17, wherein the anchor member includes a central bore centered about the longitudinal axis and extending distally from the internal drive socket to a most bottom end of the anchor member.

20. The pivotable bone anchor assembly of claim 17, wherein the planar upper surface of the proximal end portion of the anchor member is an annular top surface perpendicular to the longitudinal axis of the anchor member.

21. The pivotable bone anchor assembly of claim 17, wherein the planar upper surface entirely surrounds the internal drive socket.

22. The pivotable bone anchor assembly of claim 17, wherein the lower outer curved contact surface of the proximal end portion of the anchor member further comprises a partially spherical-shaped surface.

23. The pivotable bone anchor assembly of claim 17, wherein the curved seating surface of the internal cavity of the receiver further comprises a partially spherical-shaped surface.

24. The pivotable bone anchor assembly of claim 17, wherein the anchor member includes a neck between the proximal end portion and the anchor portion, the neck having a reduced radius that is less than a radius of an immediately adjacent portion of the anchor portion and being defined by at least one smooth curvate surface extending inwardly toward the longitudinal axis of the anchor member.

25. The pivotable bone anchor assembly of claim 17, wherein the insert includes a central through-bore sized and shaped to provide passage for a driving tool configured to engage the internal drive socket of the anchor member to drive the anchor member into the bone.

26. The pivotable bone anchor assembly of claim 17, wherein the lower surface of the insert further comprises a downwardly-opening concave curved engagement surface that is complementary with an upper outer curved contact surface located at an upper end of the proximal end portion of the anchor member above the second thread.

27. The pivotable bone anchor assembly of claim 26 wherein the upper outer curved contact surface is a partially spherical-shaped surface.

28. The pivotable bone anchor assembly of claim 26, wherein the concave curved engagement surface of the insert is a partially spherical-shaped surface.

29. The pivotable bone anchor assembly of claim 26, wherein the upper outer curved contact surface is between the second thread and the planar upper surface.

* * * * *